US012766154B2

(12) United States Patent
Banales Asurmendi et al.

(10) Patent No.: US 12,766,154 B2
(45) Date of Patent: Oct. 20, 2026

(54) URSODEOXYCHOLIC ACID DERIVATIVES FOR THE TREATMENT OF POLYCYSTIC DISEASES

(71) Applicants: UNIVERSIDAD DEL PAIS VASCO/EUSKAL HERRIKO UNIBERTSITATEA, Leioa—Vizcaya (ES); ADMINISTRACION GENERAL DE LA COMUNIDAD AUTONOMA DE EUSKADI, Vitoria—Gasteiz (ES); FUNDACIO INSTITUT D'INVESTIGACIO BIOMEDICA DE BELLVITGE (IDIBELL), Hospitalet de Llobregat (ES); UNIVERSIDAD DE SALAMANCA, Salamanca (ES)

(72) Inventors: Jesus Maria Banales Asurmendi, Donostia—San Sebastian (ES); Luis Bujanda Fernandez De Pierola, Donostia—San Sebastian (ES); Alvaro Santos Laso, Donostia—San Sebastian (ES); Fernando Pedro Cossio Mora, Leioa (ES); Ivan Rivilla De La Cruz, Leioa (ES); Francisco Javier Caballero Camino, Leioa (ES); Manel Esteller Badosa, L'Hospitalet de Llobregat (ES); Jose Juan Garcia Marin, Salamanca (ES)

(73) Assignees: ADMINISTRACION GENERAL DE LA COMUNIDAD AUTONOMA DE EUSKADI, Vitoria—Gasteiz (ES); UNIVERSIDAD DE SALAMANCA, Salamanca (ES); FUNDACIO INSTITUT D'INVESTIGACIO BIOMEDICA DE BELLVITGE (IDIBELL), Hospitalet de Llobregat (ES); UNIVERSIDAD DEL PAIS VASCO/EUSKAL HERRIKO UNIBERTSITATEA, Leioa—Vizcaya (ES)

( * ) Notice: Subject to any disclaimer, the term of this patent is extended or adjusted under 35 U.S.C. 154(b) by 0 days.

(21) Appl. No.: 18/353,525

(22) Filed: Jul. 17, 2023

(65) Prior Publication Data

US 2023/0390308 A1 Dec. 7, 2023

Related U.S. Application Data

(62) Division of application No. 16/958,429, filed as application No. PCT/ES2018/070840 on Dec. 28, 2018, now Pat. No. 11,833,160.

(30) Foreign Application Priority Data

Dec. 28, 2017 (ES) .............................. ES201731488

(51) Int. Cl.
*A61K 31/58* (2006.01)
*A61K 31/575* (2006.01)

(52) U.S. Cl.
CPC ............ *A61K 31/58* (2013.01); *A61K 31/575* (2013.01)

(58) Field of Classification Search
None
See application file for complete search history.

(56) References Cited

U.S. PATENT DOCUMENTS

| | | | |
|---|---|---|---|
| 5,646,316 | A | 7/1997 | Jacobson et al. |
| 2016/0045463 | A1 | 2/2016 | Banales et al. |

FOREIGN PATENT DOCUMENTS

| | | | |
|---|---|---|---|
| WO | 2011091213 | A2 | 7/2011 |
| WO | 2015061684 | A1 | 4/2015 |
| WO | 2016054208 | A1 | 4/2016 |

OTHER PUBLICATIONS

Scozzafava, Andrea. arbonic anhydrase inhibitors. Preparation of potent sulfonamides inhibitors incorporating bile acid tails, Bioorganic & Medicinal Chemistry Letters, vol. 12, Issue 12, 2002, (Year: 2002).*

STN File Registry. Registry No. 461657-79-6. Published 2002. Retrieved from the Internet on Nov. 14, 2025, https://www.stn.org/. (Year: 2002).*

Hedwig M.A. D'Agnolo, et al., "Ursodeoxycholic Acid in Advanced Polycystic Liver Disease: A Phase . . . ", Journal of Hepatology, vol. 65, No. 3, pp. 601-607, 2016.

Anonymous: "Ursodeoxycholic Acid as Treatment for Polycystic Liver Disease", ClinicalTrials.gov, NCT02021110, pp. 1-8, 2016.

Yusuke Iguchi, et al., Effects of Chemical Modification of Ursodeoxycholic Acid on TGR5 Activation, Biological & Pharmaceutical Bulletin (of Japan), vol. 34, No. 1, pp. 1-7, 2011.

Maria Reich, et al., "Role of the G Protein-Coupled Bile Acid . . . ", Digestive diseases, vol. 35, No. 3, pp. 235-240, 2017.

Jesus Banales, et al., "Hepatic Cystogenesis is Associated With Abnormal Expression and Location . . . ", The American Journal of Pathology, vol. 173, No. 6, pp. 1637-1646, 2008.

(Continued)

*Primary Examiner* — Lauren Wells
(74) *Attorney, Agent, or Firm* — LUCAS & MERCANTI, LLP

(57) ABSTRACT

Compounds derived from ursodeoxycholic acid of formula (I) and to methods for obtaining same, as well as the use thereof in the treatment of polycystic diseases, particularly autosomal dominant polycystic liver disease, autosomal dominant polycystic kidney disease, or autosomal recessive polycystic kidney disease.

8 Claims, 4 Drawing Sheets

(56) References Cited

OTHER PUBLICATIONS

Jesus Banales, et al., "The Camp Effectors EPAC and Protein Kinase A (PKA) Are Involved in the Hepatic . . . ", Hepatology, vol. 49, No. 1, pp. 160-174, 2009.
Ulrich Beuers, et al., New Paradigms in the Treatment of Hepatic Cholestasis: From UDCA to FXR, PXR and Beyond, Journal of Hepatology, vol. 62, pp. S25-S37, 2015.
Liudmila Cebotaru, et al., "Inhibition of Histone Deacetylase 6 Activity Reduces . . . ",Kidney International, vol. 90, pp. 90-99, 2016.
Adamo Fini, et al., "Quantitative Structure-Antimicrobial Activity Relationship . . . ", Journal of Pharmaceutical Sciences, vol. 79, No. 7, pp. 603-605, 1990.
Tom J.G. Gevers, et al., Diagnosis and Management of Polycystic Liver Disease, Nature Reviews Gastroenterology & Hepatology, vol. 10, pp. 101-108, 2013.
Sergio A. Gradllone, et al., "Cholangiocyte Cilia Express TRPV4 and Detect Changes in Luminal . . . ", PNAS, vol. 104, No. 48, pp. 19138-19143, 2007.
Sergio A. Gradilone, et al., "Activation of TRPV4 Reduces the Hyperproliferative Phenotype . . . ", Gastroenterology, vol. 139, pp. 304-314, 2010.
Sergio A. Gradilone, et al., HDAC6 is Overexpressed in Cystic Cholangiocytes and Its Inhibition Reduces Cystogenesis, The American Journal of Pathology, vol. 184, No. 3, pp. 1-9, 2014.
Kaustav Das Gupta, et al., "Histone Deacetylases in Monocyte/Macrophage Development, Activation Metabolism: Refining . . . ", Clinical & Translational Immunology, vol. 5, No. e62, pp. 1-11, 2016.
Willem-Jan Keune, et al., Rational Design of Autotaxin Inhibitors by Structural Evolution of Endogenous Modulators, Journal of Medicinal Chemistry, vol. 60, pp. 2006-2017, 2017.
Seung-Ok Lee, et al., "MICRORNA15a Modulates Expression of the Cell-Cycle Regulator . . . ", The journal of Clinical Investigation, vol. 118, No. 11, pp. 3714-3724, 2008.
Tatyana V. Masyuk, et al., "Octreotide Inhibits Hepatic Cystogenesis in a Rodent Model of Polycystic Liver Disease . . . ", Gastroenterology, vol. 132, pp. 1104-1116, 2007.
Anatoliy Masyuk, et al., "Cholangiocyte Primary Cilia Are Chemosensory Organelles That Detect Biliary Nucleotides . . . ", Am J. Physiol Gastrointest Liver Physiol, vol. 295, pp. G725-G734, 2008.
Anatoliy I. Masyuk, et al., "Biliary Exosomes Influence Cholangiocyte Regulatory Mechanisms . . . ", Am J. Physiol Gastrointest Liver Physiol, vol. 299, pp. G990-G999, 2010.
Anatoliy I. Masyuk, et al., Ciliary Subcellular Localization of TGR5 Determines the Cholangiocyte Functional Response To Bile Acid Signaling, Am J. Physiol Gastrointest Liver Physiol, vol. 304, pp. G1013-G1024, 2013.
Tatyana V. Masyuk, et al., "Centrosomal Abnormalities Characterize Human and Rodent . . . ", The American Journal of Pathology, vol. 184, No. 1, pp. 110-121, 2014.
Virpi Noponen, et al., Bile Acid-Cysteamine Conjugates: Structural Properties, Gelation, and Toxicity Evaluation, Steroids, vol. 77, pp. 193-203, 2012.
Patricia Munoz-Garrido, et al., "Ursodeoxycholic Acid Inhibits Hepatic Cystogenesis in Experimental Models . . . ", Journal of Hepatology, vol. 63, pp. 952-961, 2015.
Maria J. Perugorria, et al., Polycystic Liver Diseases: Advanced Insights Into the Molecular Mechanisms, Nature Reviews Gastroenterology & Hepatology, pp. 1-12, 2014.
Ruchika Sharma, et al., Ursodeoxycholic Acid Amides as Novel Glucocorticoid Receptor Modulators, J. Med. Chem., vol. 54, pp. 122-130, 2011.
Ruchika Sharma, et al., "Bile Acid Toxicity Structure-Activity Relationships: Correlations Between Cell Viability . . . ", Bioorganic & Medicinal Chemistry, vol. 18, pp. 6886-6895, 2010.
Kyutaro Shimizu, et al., Preparation and Chromatography of the Hydroxamic Acids of Some Bile Acids, The Journal of Biochemistry, vol. 45, No. 1, pp. 13-16, 1958.
Aura D. Urribarri, et al., "Inhibition of Metalloprotease Hyperactivity in Cystic Cholangiocytes . . . ", Gut, pp. 1-10, 2014.
Arto Valkonen, et al., Syntheses and Structural Study of Bile Acid Amidoalcohols, Steroids, vol. 73, pp. 1228-1241, 2008.
Ming Wu, et al., "Histone Deacetylases 6 Increases the Cyclic Adenosine Monophosphate . . . ", Kidney International, vol. 90, pp. 20-22, 2016.
International Search Report and Written Opinion for Corresponding International Application No. PCT/ES2018/070840 (12 Pages) (Jun. 24, 2019).
International Preliminary Report on Patentability for Corresponding International Application No. PCT/ES2018/070840 (8 Pages) (Jun. 30, 2020).
STN Registry Search of U.S. Pat. No. 5,646,316, published Jul. 8, 1997. STN registry information retrieved on Feb. 2, 2023. (Year: 1997).
Munoz-Garrido P, et al. "Ursodeoxycholic Acid Inhibits Hepatic Cystogenesis in Experimental Models of Polycystic Liver Disease", J Hepatol., vol. 63, No. 4, pp. 952-961, 2015.

* cited by examiner

URSODEOXYCHOLIC ACID DERIVATIVES FOR THE TREATMENT OF POLYCYSTIC DISEASES

CROSS-REFERENCE TO RELATED APPLICATIONS

This is a divisional of U.S. application Ser. No. 16/958,429 filed on Dec. 14, 2020, which was a 371 of PCT/ES2018/070840 filed on Dec. 28, 2018 which, in turn, claimed the priority of Spanish Patent Application No. P201731488 filed on Dec. 28, 2017, the priority of each of these applications is claimed and each of these applications are incorporated herein by reference.

FIELD OF THE INVENTION

The present invention is comprised in therapeutic treatments for polycystic liver diseases. Particularly, it relates to a therapy combining, in one and the same molecule derived from ursodeoxycholic acid, the capacity to increase intracellular $Ca^{2+}$ levels in polycystic human cholangiocytes and reduce the proliferation of said human cholangiocytes, as well as selectively inhibit the activity of the HDAC6 enzyme, mechanisms that are all involved in the development of the mentioned diseases.

BACKGROUND

Polycystic liver diseases (also referred to by their abbreviation, PLDs) are a heterogeneous group of dominantly inherited genetic disorders [autosomal dominant polycystic liver disease (ADPLD: 1:100,000) and autosomal dominant polycystic kidney disease (ADPKD: 1:1,000)] or recessively inherited genetic disorders [autosomal recessive polycystic kidney disease (ARPKD: 1:20,000)] that are characterized by the progressive development of multiple bile cysts (>20) which are the main cause of morbidity and mortality [Gevers, T. J. et al., *Nat. Rev. Gastroenterol. Hepatol.,* 2013, 10(2), 101-108; Perugorria, M. J., et al., *Nat. Rev. Gastroenterol. Hepatol.,* 2014, 11(12), 750-761]. Furthermore, a high percentage of these patients also develop polycystic kidney disease (also referred to by its abbreviation, PKD).

The surgical and/or pharmacological treatments existing today fail to improve the prognosis of these diseases, and liver transplant is presented as the only curative option. Therefore, a detailed study of the molecular mechanisms controlling the pathogenesis of polycystic liver diseases is key to enable identifying therapeutic targets at the pharmacological level.

It has previously been demonstrated that cystogenesis in PLDs is characterized by various functional alterations in polycystic bile duct cells (i.e., cholangiocytes) [Perugorria, M. J., et al., *Nat. Rev. Gastroenterol. Hepatol.,* 2014, 11(12), 750-761], such as hyperproliferation [Banales, J. M. et al., *Hepatology,* 2009, 49(1), 160-174; Munoz-Garrido, P. et al., *J. Hepatol.,* 2015, 63(4), 952-961], hypersecretion [Banales, J. M. et al., *Am. J. Pathol.,* 2008, 173(6), 1637-1646], increase in metalloproteolytic activity [Urribarri, A. D. et al., Gut, 2014, 63(10), 1658-1667], change in the expression of microRNAs [Lee, S. O. et al., *J. Clin. Invest.,* 2008, 118(11), 3714-3724], and morphological and functional alterations of the primary cilium [Masyuk, T. V. et al., *Am. J. Pathol.,* 2014, 184(1), 110-121] (i.e., a specific sensory organelle of cholangiocytes in the liver) [Gradilone, S. A. et al., *Proc. Natl. Acad. Sci. USA,* 2007, 104(48), 19138-19143; Masyuk, A. I., et al., *Am. J. Physiol. Gastrointest. Liver Physiol.,* 2008, 295(4), G725-734; Masyuk, A. I. et al., *Am. J. Physiol. Gastrointest. Liver Physiol.,* 2013, 304(11), G1013-1024; Masyuk, A. I. et al., *Am. J. Physiol. Gastrointest. Liver Physiol.,* 2010, 299(4), G990-999].

Furthermore, it has been proven that these pathological processes are intracellularly mediated by an increase in the levels of cyclic 3',5'-adenosine monophosphate (cAMP) and a decrease in calcium ($Ca^{2+}$), with the regulation thereof being considered potentially therapeutic [Perugorria, M. J. et al., *Nat. Rev. Gastroenterol. Hepatol.,* 2014, 11(12), 750-761; Munoz-Garrido, P. et al., *J. Hepatol.,* 2015, 63(4), 952-961; Gradilone, S. A. et al., *Gastroenterology,* 201, 139(1), 304-314; Masyuk, T. V. et al., *Gastroenterology,* 2007, 132(3), 1104-1116]. In this sense, it has recently been proven that normalization of intracellular $Ca^{2+}$ levels in polycystic cholangiocytes with ursodeoxycholic acid (known by its abbreviation, UDCA) is capable of partially blocking liver cystogenesis in various experimental models of PLD [Munoz-Garrido, P. et al., *J. Hepatol.,* 2015, 63(4), 952-961].

UDCA is an endogenous bile acid with choleretic and hepatoprotective properties found at a low concentration in the human body and the chronic administration thereof leads to therapeutic benefits in cholestatic liver diseases, such as primary biliary cholangitis (PBC) [Beuers, U. et al., J. Hepatol., 2015, 62(1 Suppl), S25-37]. The oral administration of UDCA is well tolerated and safe, and is the only internationally approved therapy for the chronic treatment of PBC. Based on all this data, an international, multicenter, phase II clinical trial (see clinicaltrials.gov, identifier: NCT02021110) was started, in which the therapeutic potential of the chronic treatment of PLD patients with UDCA was evaluated. In that sense, it has recently been proven [D'Agnolo HMA. et al., J. Hepatol., 2016, 65(3), 601-607] that UDCA inhibits the growth of liver cysts in patients with polycystic kidney disease (i.e., ADPKD) that are highly symptomatic (total liver volume >2.5 liters), and furthermore causes a significant improvement in its symptomatology. Nevertheless, the administration of UDCA does not seem to show any benefit in reducing the total liver volume in patients with advanced polycystic liver disease (ADPLD). It is therefore proposed that additional studies are required to determine if patients with ADPKD and ADPLD respond differently to treatment with UDCA.

Given that UDCA has a partial therapeutic effect in animal models and patients with PLD, the study of pharmacological therapies which act against different signaling pathways involved in the pathogenesis of these diseases is key to thereby enable effectively blocking their development and/or progression.

On the other hand, it has been proven that the growth of liver cysts in PLDs is mediated, in part, by the cytoplasmic overexpression of HDAC6 (histone deacetylase 6), which promotes the deacetylation of the structural protein, α-acetylated-tubulin, in the primary cilia of cholangiocytes [Gradilone, S. A. et al., *Am. J. Pathol.,* 2014, 184(3), 600-608]. This causes structural and functional malformations of these organelles which promote cell proliferation.

In that sense, it has been proven that chronic administration of pharmacological HDAC6 inhibitors (i.e., tubastatin, tubacin, and ACY-1215) causes a decrease in the proliferation of cholangiocytes derived from patients with ADPKD and partially blocks the growth of liver cysts in experimental models (i.e., in vitro and in vivo) of PLD.

Furthermore, Wu, M. et al. [*Kidney International,* 2016, 90(1), 20-22] mention that the mutation of a gene in polycystic kidney disease leads to a decrease in the intracellular $Ca^{2+}$ concentration, as well as an increase in cyclic AMP levels, which is linked to the overexpression of HDAC6. Based on the foregoing, it is proposed that calcium and cyclic AMP regulate HDAC6 expression and activity.

In this sense, Cebotaru, L. et al. [*Kidney International,* 2016, 90(1), 90-97] observed that tubacin prevents the formation of cysts in MDCK cells (an in vitro model of cystogenesis) and that treatment with said compound regulates cyclic AMP levels, therefore inhibiting cell proliferation. It is furthermore observed in testing with an animal model of ADPKD that tubacin reduces the growth of kidney cysts by means of inhibiting the epithelial cells covering the cysts, improving kidney function.

Document WO2015/061684 also describes HDAC6 inhibitors which respond to different structures, some of which are previously known in the literature (WO2011/091213), for the treatment of polycystic diseases, particularly those derived from ARPKD (caused by the mutation of the Pkhd1 gene) and ADPKD disease (caused by the mutation of the Pkd1 and Pkd2 genes). Among the groups of patients to be treated with these compounds, those with mutations in at least one of the ADPLD-causing PRKCSH and Sec63 genes are also included. Nevertheless, the examples provided were carried out in animal models of ARPKD.

However, the clinical study of the therapeutic efficacy of these pharmacological HDAC6 inhibitors is compromised by the peripheral toxicity of commercial HDAC6 inhibitors. To that end, there is a need to search for new HDAC6 inhibitors having a more selective vectorization towards the cells of the bile ducts and less peripheral toxicity.

BRIEF DESCRIPTION OF THE INVENTION

The authors of the present invention have developed new ursodeoxycholic acid (UDCA) derivatives which maintain the intrinsic, beneficial calcium-regulating properties of UDCA itself and act at the same time as selective HDAC6 inhibitors.

In that sense, the results of the experiments carried out with these new UDCA derivatives have clearly shown that these derivatives increase intracellular $Ca^{2+}$ levels in polycystic human cholangiocytes in culture in a manner similar to UDCA, but they furthermore induce a decrease in the proliferation of said human cholangiocytes in a dose-dependent manner and at a higher magnitude than UDCA. On the other hand, the chemical entities of this invention have shown a selective inhibition of HDAC6 activity that is at least comparable with other commercial HDAC inhibitors such as trichostatin.

All this experimental data would clearly show that the administration of these new compounds in patients with polycystic liver diseases may have significant therapeutic value in the treatment thereof.

A first aspect of the present invention therefore relates to a compound of formula (I):

(I)

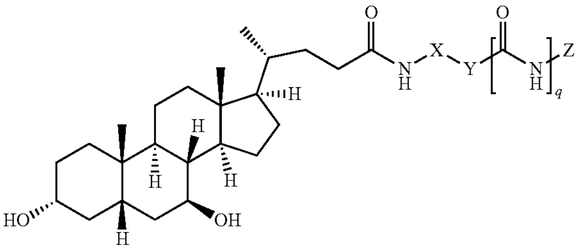

where:

X is a —$(CHR_1)_p$ group, where $R_1$ is hydrogen, or a $C_1$-$C_6$ alkyl group, or a $C_6$-$C_{10}$ aryl group, and p is 0 or 1;

Y is selected from:

a single bond;

—$(CH_2)_n$, with n being 1, 2, 3, 4, or 5;

arylidene or heteroarylidene, connected with the rest of the molecule by means of (1,3) or (1,4) bonds;

—C(O)—N(H)—$CH_2$ (Ar)—; and

—Ar—C(O)—N(H)—$CH_2$—(Ar)—;

where Ar means arylidene;

q is 0 or 1;

Z is selected from OH, SH, and optionally substituted aryl, or a pharmaceutically acceptable stereoisomer, salt, or solvate thereof, for use in the treatment of polycystic diseases.

A second aspect of the invention relates to a compound of formula (I'):

(I')

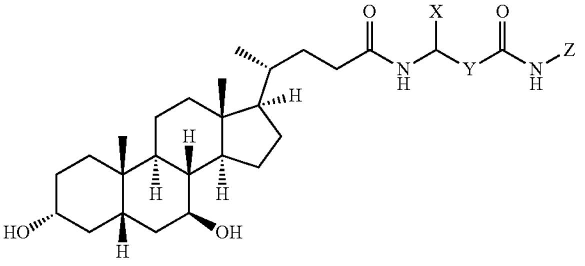

where:

X is hydrogen, a $C_1$-$C_6$ alkyl group, or a $C_6$-$C_{10}$ aryl group;

Y is selected from:

a single bond;

—$(CH_2)_n$, with n being 1, 2, 3, 4, or 5;

arylidene or heteroarylidene, connected with the rest of the molecule by means of (1,3) or (1,4) bonds;

—C(O)—N(H)—$CH_2$(Ar)—; and

—Ar—C(O)—N(H)—$CH_2$—(Ar)—;

where Ar means arylidene;

and

Z is selected from OH and optionally substituted aryl, or a pharmaceutically acceptable stereoisomer, salt, or solvate thereof.

An additional aspect of the invention relates to a process for obtaining compounds of formula (I') which comprises reacting ursodeoxycholic acid of formula (II):

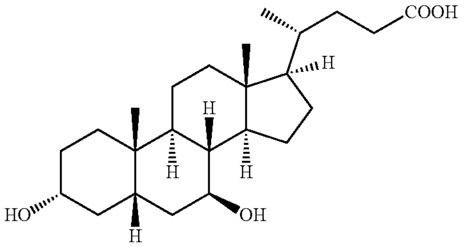
(II)

with a compound of formula (III'):

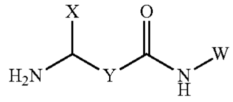
(III')

where X and Y are as defined above and W is a precursor group of groups Z defined above, and subsequently transforming groups W into the corresponding groups Z of formula (I).

An additional aspect of the invention relates to a pharmaceutical composition comprising a compound of formula (I') as defined above, or a diastereomer, or a salt or solvate thereof, and a pharmaceutically acceptable excipient or vehicle.

The invention furthermore relates to a compound of formula (I') as defined above or a diastereomer, or a salt or solvate thereof, for use as a medicinal product.

DETAILED DESCRIPTION OF THE INVENTION

Figure 1:
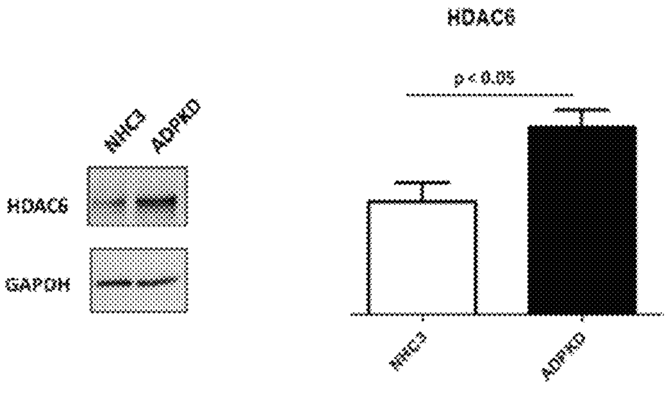
FIG. 1 shows the representative immunoblot and relative quantification of the expression of HDAC6 in normal and polycystic human cholangiocytes.

As mentioned above, a first aspect of the present invention relates to an ursodeoxycholic acid derivative, specifically a compound of formula (I):

(I)

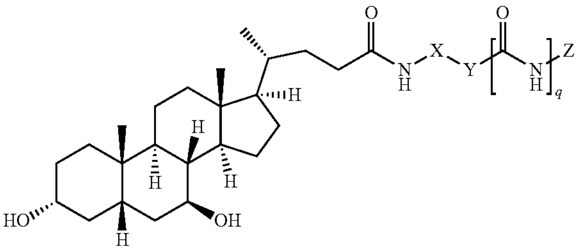

where:

X is a —$(CHR_1)_p$ group, where $R_1$ is hydrogen, or a $C_1$-$C_6$ alkyl group, or a $C_6$-$C_{10}$ aryl group, and p is 0 or 1;

Y is selected from:

a single bond;

—$(CH_2)_n$, with n being 1, 2, 3, 4, or 5;

arylidene or heteroarylidene, connected with the rest of the molecule by means of (1,3) or (1,4) bonds;

—C(O)—N(H)—$CH_2$(Ar)—; and

—Ar—C(O)—N(H)—$CH_2$—(Ar)—;

where Ar means arylidene;

q is 0 or 1;

Z is selected from OH, SH, and optionally substituted aryl, or a pharmaceutically acceptable stereoisomer, salt, or solvate thereof, for use in the treatment of polycystic diseases.

In the context of the present invention, the following terms have the meaning that is described in detail below.

"$C_1$-$C_6$ alkyl" refers to a radical that has a linear or branched hydrocarbon chain consisting of 1 to 6 carbon atoms, preferably 1 to 3 carbon atoms, does not contain any unsaturation, and is bound to the rest of the molecule by means of a single bond, for example, methyl, ethyl, n-propyl, i-propyl, n-butyl, t-butyl, n-pentyl, etc. The $C_1$-$C_6$ radical alkyl can optionally be substituted with one or more substituents, particularly, with an aryl or heteroaryl terminal group.

"$C_6$-$C_{10}$ aryl" refers to a radical which has an aromatic ring comprising 6 to 10 carbon atoms, even more, particularly 6 carbon atoms. According to a particular embodiment, aryl is a phenyl, naphthyl, indenyl, phenanthryl, or anthracyl radical, preferably phenyl or naphthyl radical. The radical aryl can optionally be substituted with one or more substituents, particularly, with C(O)NHOH; linear or branched $C_1$-$C_4$ alkyl; SH; $NH_2$; $C_6$-$C_{10}$ aryl; $C_5$-$C_6$ heteroaryl.

"Arylidene" refers to an aromatic ring system which comprises 6 to 10 carbon atoms, even more particularly 6 carbon atoms, and is bound to the molecule through two bonds. According to a particular embodiment, arylidene is a phenylene, naphthylene, indenylene group, preferably a radical phenylene group bound to the molecule by means of (1,3) or (1,4) bonds.

"Heteroarylidene" refers to a stable, 3- to 10-membered, aromatic ring system, preferably a 5- or 6-membered aromatic ring, comprising carbon atoms, and from one to five heteroatoms selected from the group consisting of nitrogen, oxygen, and sulfur, preferably one or two heteroatoms. The heteroarylidene group is bound to the molecule through two bonds. Examples of such heteroarylidene include, but are not limited to, radicals derived from benzimidazole, benzothiazole, furan, thiophene, pyrrole, pyridine, pyrimidine, isothiazole, imidazole, indole, purine, quinoline, or thiadiazole. Preferably, it is a radical derived from furan which is bound to the molecule by means of (1,3) bonds.

The compounds of formula (I) can be in the form of salts, preferably pharmaceutically acceptable salts, or in the form of solvates.

The expression "pharmaceutically acceptable salts" refers to salts which, when administered to the recipient, may (directly or indirectly) provide a compound like the one described herein. "Pharmaceutically acceptable" preferably refers to compositions and molecular entities which are physiologically tolerable and do not normally cause an allergic reaction or a similar unfavorable reaction, such as upset stomach, dizziness, and the like, when administered to a human being or animal. Preferably, the expression "pharmaceutically acceptable" means that it is approved by a state or federal government regulatory agency or included in the United States Pharmacopeia or another pharmacopeia generally recognized for use in animals, and more particularly in human beings.

The salts can be prepared by means of methods known in the art. For example, the pharmaceutically acceptable salts of compounds provided in the present document are synthesized from the original compound containing basic residues by means of conventional chemical methods. In general, such salts are prepared, for example, by reacting the free base forms of these compounds with the suitable base or acid in water, or in an organic solvent, or in a mixture of the two. In general, non-aqueous media such as ether, ethyl acetate, ethanol, isopropanol, or acetonitrile, are preferred. Examples of acid addition salts include mineral acid addition salts such as, for example, hydrochloride, hydrobromide, hydroiodide, sulfate, nitrate, phosphate, and organic acid addition salts such as, for example, acetate, maleate, fumarate, citrate, oxalate, succinate, tartrate, malate, mandelate, methanosulfonate, and p-toluenesulfonate salts. Examples of base addition salts include inorganic salts such as, for example, sodium, potassium, calcium, ammonium, magnesium, aluminum, and lithium, and organic salts such as, for example, ethylenediamine, ethanolamine, N,N-dialkylenethanolamine, triethanolamine, glucamine, and basic amino acid salts.

The term "solvate" according to this invention must be understood to mean any form of the active compound according to the invention having another molecule (most probably a polar solvent) bound thereto by means of a non-covalent bond. Examples of solvates include hydrates and alcoholates, for example methanolate. The compounds of the invention can be in crystalline form, as free compounds or solvates. Solvation methods are known in the art.

In a particular embodiment, in the compounds of formula (I) p is 1. In another particular embodiment, p is 0.

In a particular embodiment, in the compounds of formula (I) q is 1, and in another particular embodiment, q is 0.

In a particular embodiment, in the compounds of formula (I) X is $-(CH_2)_p-$, where p is 1.

In another particular embodiment, X is $CHR_1$, where $R_1$ is a $C_1$-$C_6$ alkyl group or $C_6$-$C_{10}$ aryl group with an R or S configuration. More preferably, $R_1$ is a $C_1$-$C_6$ alkyl group with an R or S configuration, even more preferably it is a $CH_3$ group.

In another particular embodiment, in the compounds of formula (I) Y is a single bond. More particularly, if Y is a single bond, then p is 0. Even more particularly, in the event that Y is a single bond, p is 0 and q is 0.

In another particular embodiment, in the compounds of formula (I) Y is arylidene or heteroarylidene, preferably a radical derived from furan.

In an even more particular embodiment, when Y is arylidene or heteroarylidene, p is 1. Even more preferably, in the event that Y is arylidene or heteroarylidene, p is 1 and $R_1$ is hydrogen.

In another particular embodiment, in the compounds of formula (I) Y is $-(CH_2)_n$, where n is 1, 2, 3, 4, or 5, preferably 1, 2, 3, or 4.

In another particular embodiment, q is 1.

In another particular embodiment, in the compounds of formula (I) Y is $-(CH_2)_n-$ and q is 1. Even more preferably, in the event that Y is $-(CH_2)_n-$, q is 1 and Z is OH.

In another particular embodiment, in the compounds of formula (I) Z is OH, SH, or an aryl optionally substituted by at least one of $NH_2$, SH, and a phenyl. In a more preferred embodiment, Z is OH.

In a preferred embodiment, the compounds of formula (I) are selected from the following:

(Ia)

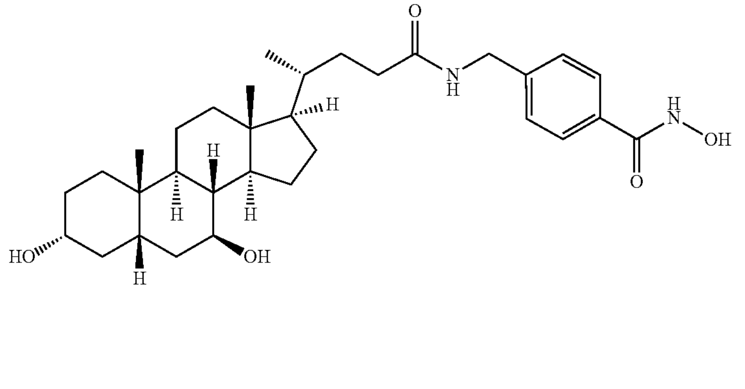

-continued
(Ib)
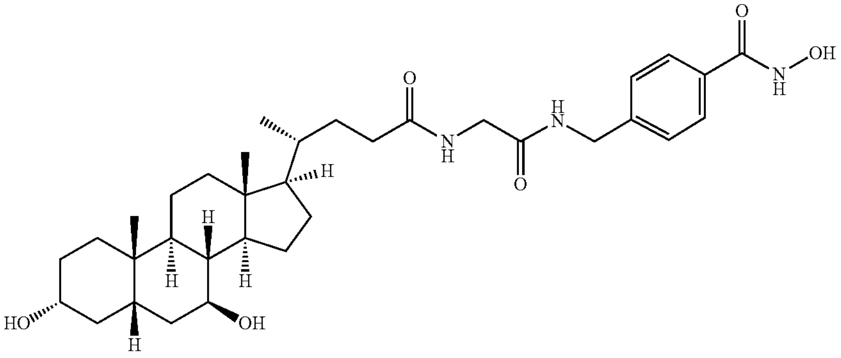
(Ic)
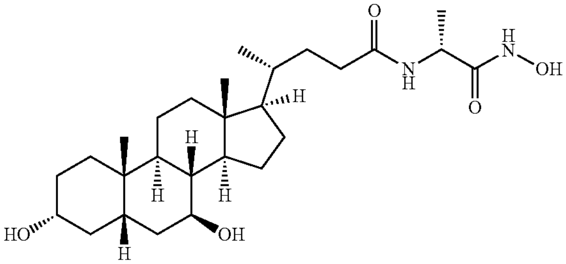
(Id)
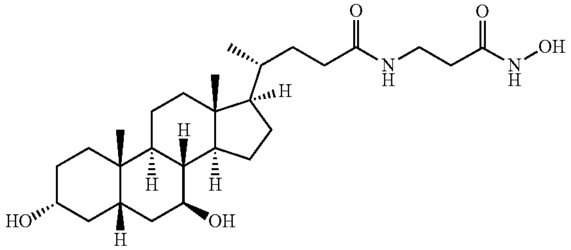
(Ie)
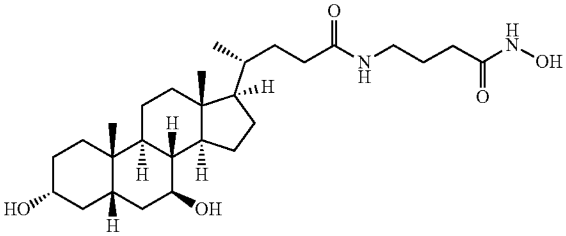
(If)
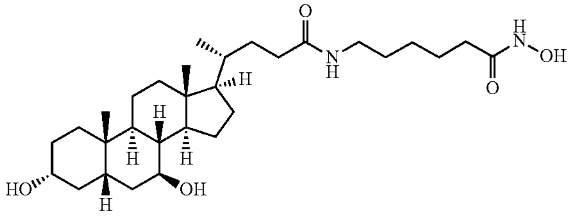
(Ig)
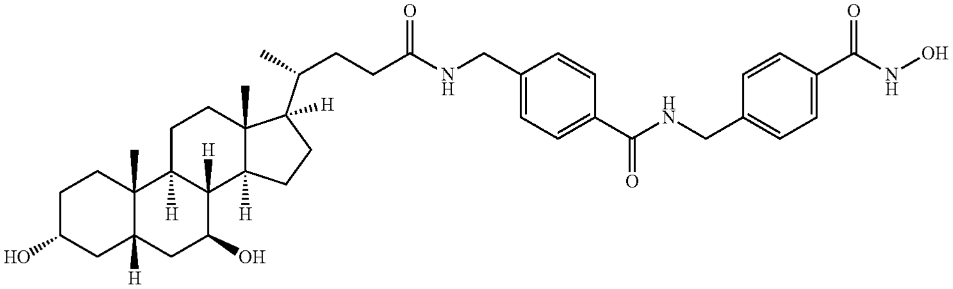
(Ih)
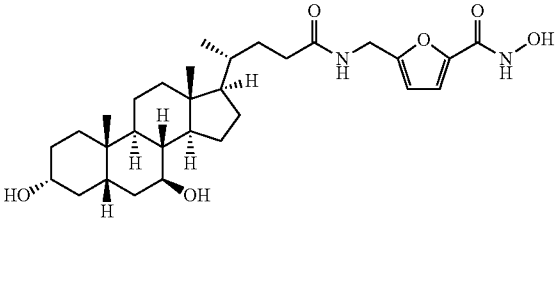
(Ii)
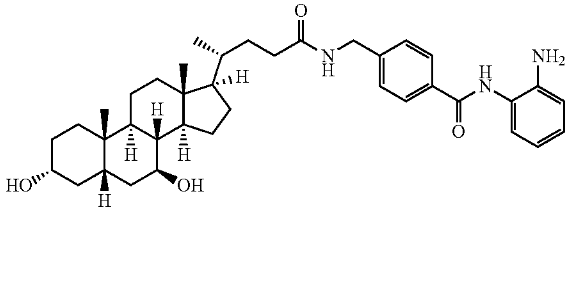

-continued (Ij)

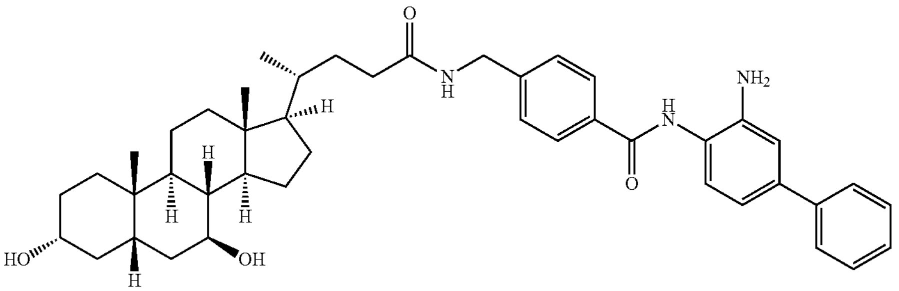

(Ik)

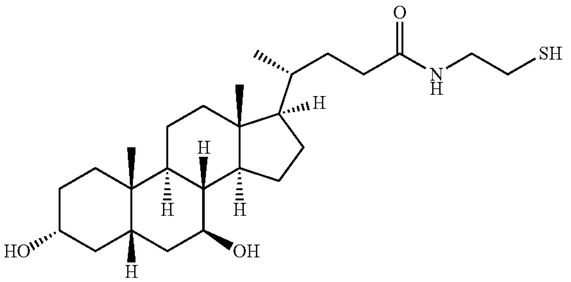

(Il)

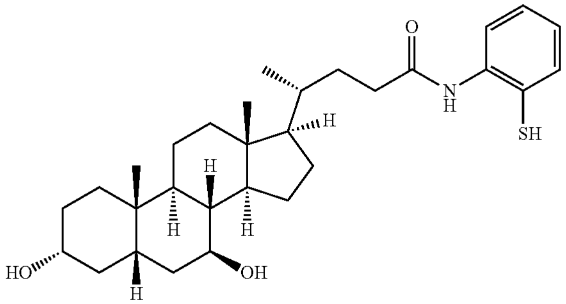

or from pharmaceutically acceptable stereoisomers, salts, or solvates thereof.

The present invention also describes a method for the treatment of polycystic disease which comprises administering a compound of formula (I) or a stereoisomer, or a salt or solvate thereof, to a patient in need of said treatment.

The term “treatment” or “treating” in the context of this specification means the administration of a compound or a pharmaceutical composition according to the invention to prevent, improve, or eliminate the disease or one or more symptoms associated with said disease. “Treatment” also comprises preventing, improving, or eliminating the physiological sequelae of the disease.

Polycystic disease must be understood as a disease characterized by the formation of cysts.

Polycystic diseases may include cholangiopathies, a group of liver diseases of different etiologies in which cholangiocytes are the target cells. Particularly, these diseases present or are mediated by a decrease in intracellular $Ca^{2+}$ levels in said cholangiocytes, as well as an increase in the proliferation of said cholangiocytes. The experimental data that was provided showed that the compounds of formula (I) of the present invention allow regulating intracellular $Ca^{2+}$ levels in polycystic human cholangiocytes, and furthermore induce a decrease in the proliferation of said cholangiocytes.

Therefore, the compounds of the invention can be used to inhibit the proliferation of cholangiocytes.

In a particular embodiment, the cholangiopathy is polycystic liver disease. Said disease may present alone or together with polycystic kidney disease.

Therefore, in a particular embodiment, the polycystic disease is selected from polycystic kidney disease, polycystic liver disease, and a combination of both.

In a particular embodiment, the compounds of formula (I) are used in the treatment of patients having one or more mutations in at least one of the PRKCSH (Protein Kinase C Substrate 80K-H) and Sec63 genes. These mutations cause polycystic liver disease without the kidney being involved. Said disease is commonly known as autosomal dominant polycystic liver disease, abbreviated as ADPLD. Therefore, in a particular embodiment, the polycystic disease is autosomal dominant polycystic liver disease.

In another particular embodiment, the compounds of formula (I) are used in the treatment of patients having one or more mutations in at least one of the Pkd1 and Pkd2 genes which encode cilium-associated proteins polycystin-1 (PC1) and polycystin-2 (PC2), and cause cystic degeneration of the liver and kidneys in autosomal dominant polycystic kidney disease, abbreviated as ADPKD. Therefore, in a particular embodiment, the polycystic disease is autosomal dominant polycystic kidney disease.

In another particular embodiment, the compounds of formula (I) are used in the treatment of patients having one or more mutations in the Pkhd1 gene which is associated with autosomal recessive polycystic kidney disease. Therefore, in a particular embodiment, the polycystic disease is autosomal recessive polycystic kidney disease.

An additional aspect of the invention relates to a compound of formula (I'):

(I')

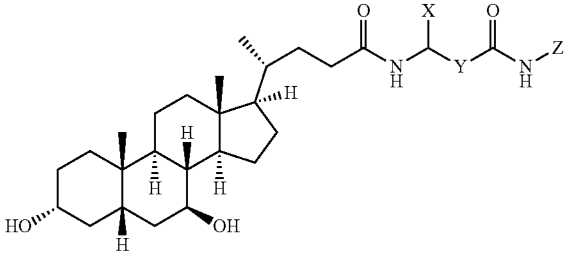

where:

X is hydrogen, a $C_1$-$C_6$ alkyl group, or a $C_6$-$C_{10}$ aryl group;

Y is selected from:

a single bond;

—$(CH_2)_n$, with n being 1, 2, 3, 4, or 5;

arylidene or heteroarylidene, connected with the rest of the molecule by means of (1,3) or (1,4) bonds;

—C(O)—N(H)—$CH_2$(Ar)—; and

—Ar—C(O)—N(H)—$CH_2$—(Ar)—;

where Ar means arylidene;

and

Z is selected from OH and optionally substituted aryl, or a pharmaceutically acceptable stereoisomer, salt, or solvate thereof.

In a particular embodiment, in the compounds of formula (I') X is hydrogen.

In another particular embodiment, X is a $C_1$-$C_6$ alkyl group or $C_6$-$C_{10}$ aryl group with an R or S configuration. More preferably, X is a $C_1$-$C_6$ alkyl group with an R or S configuration, even more preferably it is a $CH_3$ group.

In another particular embodiment, in the compounds of formula (I') Y is a single bond.

In another particular embodiment, in the compounds of formula (I') Y is arylidene or heteroarylidene, preferably a radical derived from furan.

In an even more particular embodiment, when Y is arylidene or heteroarylidene, X is hydrogen.

In another particular embodiment, in the compounds of formula (I') Y is —$(CH_2)_n$, where n is 1, 2, 3, or 4.

In another particular embodiment, in the compounds of formula (I') Z is OH or an aryl optionally substituted by at least one of $NH_2$ and a phenyl. In a more preferred embodiment, Z is OH.

In a preferred embodiment, the compounds of formula (I') are selected from the following:

(Ia)

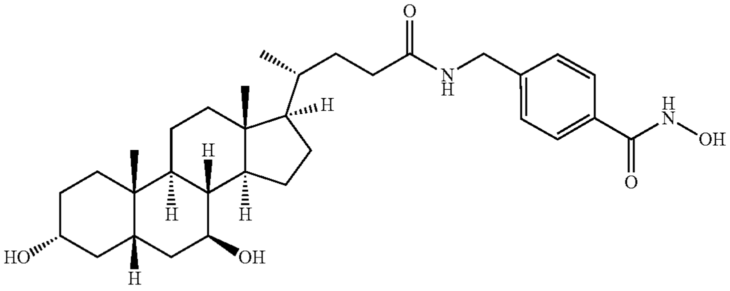

(Ib)

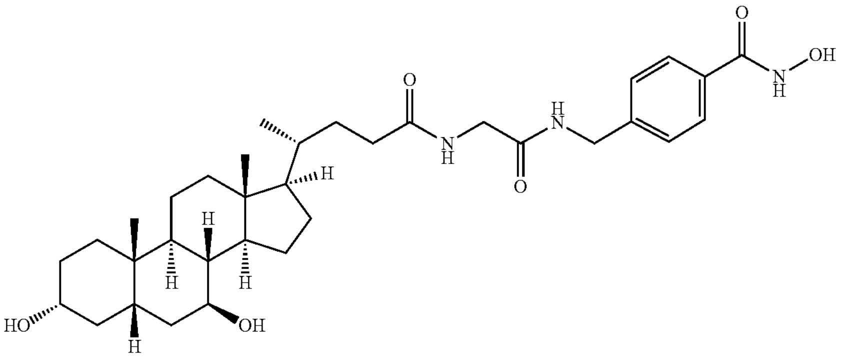

(Ic)

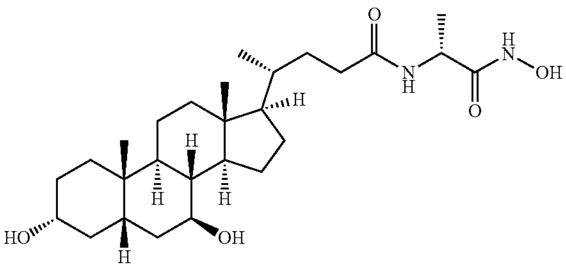

(Id)

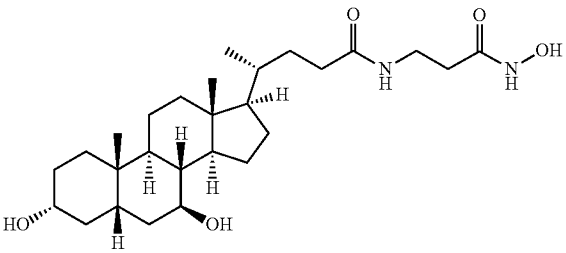

-continued (Ie)

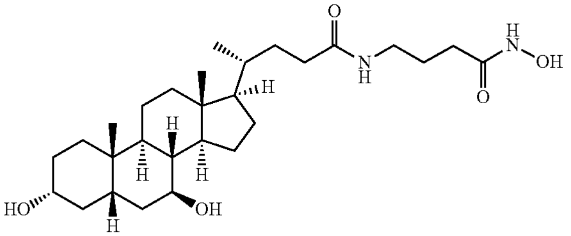

(If)

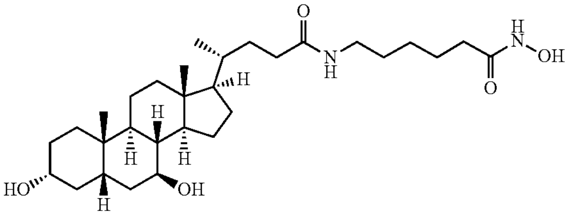

(Ig)

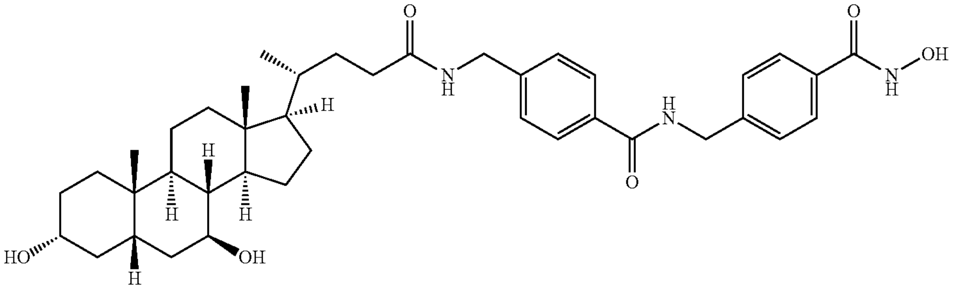

(Ih)

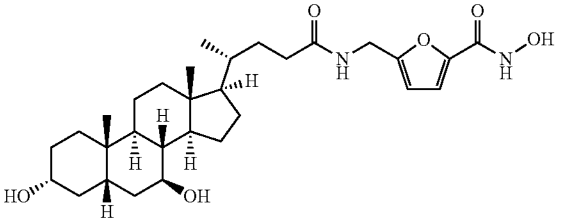

(Ii)

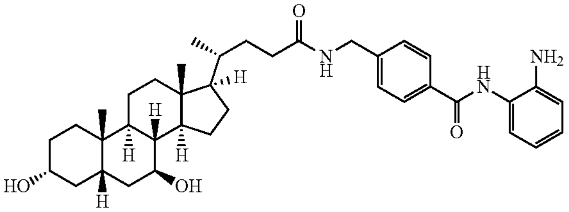

(Ij)

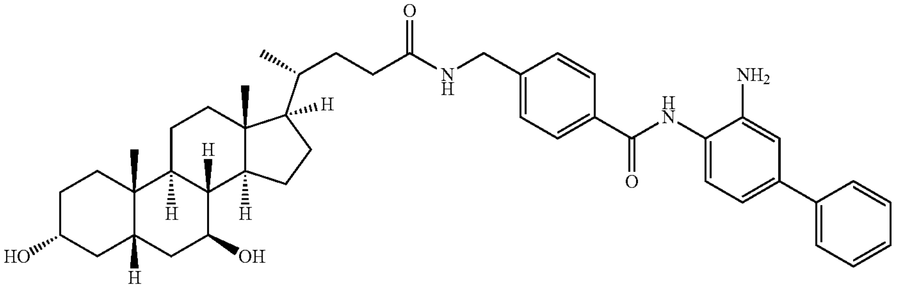

An additional aspect of the invention relates to a process for obtaining a compound of formula (I'), wherein said process comprises:

reacting ursodeoxycholic acid of formula (II):

(II)

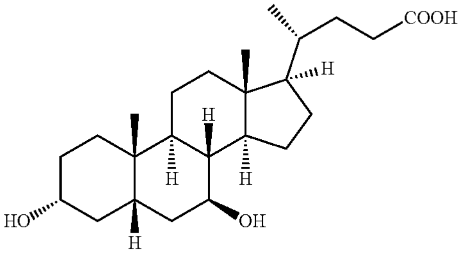

with a compound of formula (III'):

(III')

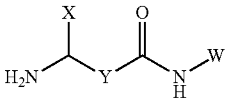

where:

X is hydrogen, or a $C_1$-$C_6$ alkyl group, or a $C_6$-$C_{10}$ aryl group;

Y is selected from:

a single bond;

—$(CH_2)_n$, with n being 1, 2, 3, 4;

arylidene or heteroarylidene, connected with the rest of the molecule by means of (1,3) or (1,4) bonds;

—C(O)—N(H)—$CH_2$(Ar)—; and

—Ar—C(O)—N(H)—$CH_2$—(Ar)—;

where Ar means arylidene;

and where W is a precursor group of groups Z defined above, and subsequently transforming groups W into the corresponding groups Z of formula (I').

In a preferred embodiment, W is an alkoxy group such as, for example, methoxy, ethoxy, or Cert-butoxy, as well as the corresponding acids.

Another aspect of the invention relates to a pharmaceutical composition comprising at least one compound of formula (I') as defined above, or a stereoisomer or a salt or solvate thereof, and at least one pharmaceutically acceptable excipient or vehicle.

Examples of pharmaceutical compositions include any solid composition (tablets, pills, capsules, granules, etc.) or liquid composition (solutions, suspensions, or emulsions) for oral, topical, or parenteral administration.

In a preferred embodiment, the pharmaceutical compositions are oral compositions. The dosage forms suitable for oral administration may include tablets and capsules and contain conventional excipients known in the art, such as binding agents, for example, syrup, gum arabic, gelatin, sorbitol, tragacanth, or polyvinylpyrrolidone; fillers, for example, lactose, sugar, cornstarch, calcium phosphate, sorbitol, or glycine; lubricants for preparing tablets, for example, magnesium stearate; disintegrants, for example, starch, polyvinylpyrrolidone, sodium starch glycolate, or microcrystalline cellulose; or pharmaceutically acceptable wetting agents such as sodium lauryl sulfate.

The solid oral compositions can be prepared by means of conventional methods of mixing, filling, or preparing tablets. Repeated mixing operations can be used to distribute the active ingredient throughout all the compositions using large amounts of fillers. Such operations are conventional in the art. The tablets can be prepared, for example, by means of dry or wet granulation, and they can optionally be coated according to methods that are well known in normal pharmaceutical practice, particularly with an enteric coating.

The pharmaceutical compositions can also be adapted for parenteral administration, such as sterile solutions, suspensions, or lyophilized products in the form of suitable unit dose. Suitable excipients such as bulking agents, buffering agents, or surface active agents can be used.

The mentioned formulations will be prepared using common methods such as those described or referred to in the Spanish and United States Pharmacopeias and similar reference texts.

In general, the effective administered amount of a compound of the invention will depend on the relative efficacy of the chosen compound, the severity of the disorder being treated, and the weight of the patient. However, the active compounds will usually be administered one or more times a day, for example, 1, 2, 3, or 4 times a day, with typical total daily doses in the range of 0.01 to 1000 mg/kg/day.

The compounds of the present invention can be used with at least one other drug to provide a combination therapy. The at least one other drug can be part of the same composition, or can be provided as a separate composition for administration at the same time or at different times.

Another aspect of the present invention relates to a compound of general formula (I'), or a stereoisomer or a salt or solvate, for use as a medicinal product.

EXAMPLES

The following methods A to C describe the processes for obtaining compounds used in the invention.

Method A:

Method A represents a process for preparing compounds of general formula (I) or (I') which comprises reacting a mixture made up of:

a) ursodeoxycholic acid of formula (II):

(II)

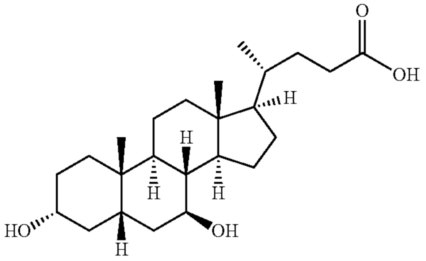

b) a compound of formula (III) or (III'):

(III)

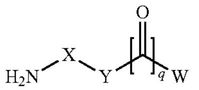

(III')

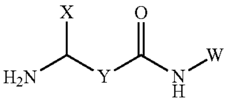

where q is 0 or 1;

X and Y for formula (III) are as defined above for formula (I);

X and Y for formula (III') are as defined above for formula (I');

W is a precursor group of groups Z defined for the compounds of formula (I) and (I');

c) a carboxyl group activation reagent;

d) an organic or inorganic base; and e) a tertiary amine, which is selected from cyclic or acyclic aliphatic amines with between 1 and 10 C atoms, and aromatic alkanes with between 9 and 15 carbon atoms.

For the purpose of the invention, the reaction can be carried out by means of the mixture formed by the five compounds [(a) to (e)] listed above and can be performed by adding one of the components to the previous mixture of the other four compounds in the organic solvent and at the temperature of −85° C. to +25° C., preferably at temperatures close to 0° C. After the last addition of one of the five components listed above, the reaction is left to reach room temperature and the progression thereof is monitored by means of TLC. Once the coupling reaction has ended, the final compound, an ester, is reacted with HCl $NaHCO_3$ (saturated aqueous solution) and NaCl (saturated aqueous solution), and dried on $MgSO_4$. Finally, the solvent is removed under vacuum. The product thus obtained is purified by means of column chromatography.

Method B:

Method B represents a process for preparing compounds of general formula (I) also from the five compounds mentioned in Method A. Likewise, the reaction mixture formed by the elements listed above can be made by adding one of the components to the previous mixture of the other components in an organic solvent and at the temperature of −85° C. to +25° C., preferably at temperatures close to 0° C. Once the addition has ended, the reaction is left to reach room temperature. The progression of the reaction was followed by thin layer chromatography. Once the coupling reaction is completed, the ester obtained is dissolved in an organic solvent and reacted with the mixture of lithium or sodium hydroxide, dimethoxyethane, and water, at temperatures comprised between −4° C. and +25° C., therefore yielding, after the corresponding treatment, compounds of general formula (I).

Method C:

Method C represents a process for preparing compounds of general formula (I) also from the five compounds mentioned in Method A. Likewise, the reaction mixture formed by the elements listed above can be made by adding one of the components to the previous mixture of the other components in an organic solvent and at the temperature of −85° C. to +25° C., preferably at temperatures close to 0° C. Once the addition has ended, the reaction is left to reach room temperature. The progression of the reaction is followed by thin layer chromatography. Once the coupling reaction is completed, the ester obtained is added to a mixture of phenolphthalein and hydroxylamine hydrochloride in the presence of excess sodium methoxide in methanol as a solvent. Once the reaction is completed, the corresponding compounds of formula (I) are obtained, after the necessary treatment in each case.

To facilitate understanding of the preceding ideas, several examples for carrying out the present invention are described below. Said examples are merely illustrative.

Example 1: Preparation of methyl 4-(((R)-4-((3R,5S,7S,8R,9S,10S,13R,14S,17R)-3,7-dihydroxy-10,13-dimethylhexadecahydro-1H-cyclopenta[a]phenanthren-17-yl)pentanamide)methyl)benzoate

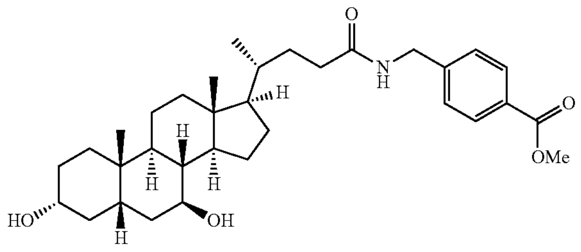

This compound was prepared following method A described above.

Methyl 4-(aminomethyl)benzoate hydrochloride (201.7 mg, 1 mmol), TBTU (385.3 mg, 1.2 mmol) were added to a solution of ursodeoxycholic acid (392.6 mg, 1 mmol) in DMF (2.5 ml). The solution was cooled to 0° C. in an inert atmosphere and a solution of $Et_3N$ in DMF ($Et_3N$ (1.1 ml, 3.26 M)) was added dropwise. The progression of the reaction was followed by thin layer chromatography. The reaction mixture was kept under stirring for 3 hours. The solvent was then evaporated at reduced pressure, and the residue was dissolved in ethyl acetate (20 ml) and the resulting solution was washed with HCl (3×10 ml solution), $NaHCO_3$ (3×10 ml, saturated aqueous solution), and NaCl (2×10 ml, saturated aqueous solution), and dried on $MgSO_4$. Finally, the solvent was removed under vacuum. The product thus obtained was purified by means of column chromatography using a 10:1 (v/v) dichloromethane:methanol mixture as mobile phase. White solid.

Yield 84%; Melting point 114-116° C.; IR 3293, 2927, 2862, 1720, 1650, 1277, 1106 $cm^{-1}$; $^{1}H$ NMR (400 MHz, DMSO-$d_6$)δ: 8.39 (t, J=6.0 Hz, 1H), 7.90 (d, J=8.2 Hz, 2H), 7.37 (d, J=8.1 Hz, 2H), 4.49 (d, J=4.4 Hz, 1H), 4.32 (dd, J=6.0, 2.7 Hz, 2H), 3.88 (d, J=6.7 Hz, 1H), 3.83 (s, 3H), 3.29 (s, 2H), 2.28-2.02 (m, 2H), 1.96-1.61 (m, 6H), 1.55-1.25 (m, 10H), 1.25-0.93 (m, 7H), 0.93-0.83 (m, 7H), 0.60 (s, 3H); $^{13}C$ NMR (101 MHz, DMSO-$d_6$) δ 172.77, 166.06, 145.50, 129.16, 128.06, 127.26, 69.77, 69.48, 54.77, 52.01, 43.10, 43.01, 42.22, 41.80, 39.86, 38.78, 37.74, 37.28, 34.93, 34.86, 33.76, 32.42, 31.67, 30.25, 28.20, 26.71, 23.32, 20.89, 18.44, 12.00; HRMS (ESI) for $C_{33}H_{49}NO_5Na$, calculated $[M+Na]^+$: 562.3509. Obtained: 562.3515.

Example 2: Preparation of methyl 4-((2-((R)-4-((3R,5S,7S,8R,9S,10S,13R,14S,17R)-3,7-dihydroxy-10,13-dimethylhexadecahydro-1H-cyclopenta[a]phenanthren-17-yl)pentanamide)acetamido)methyl)benzoate

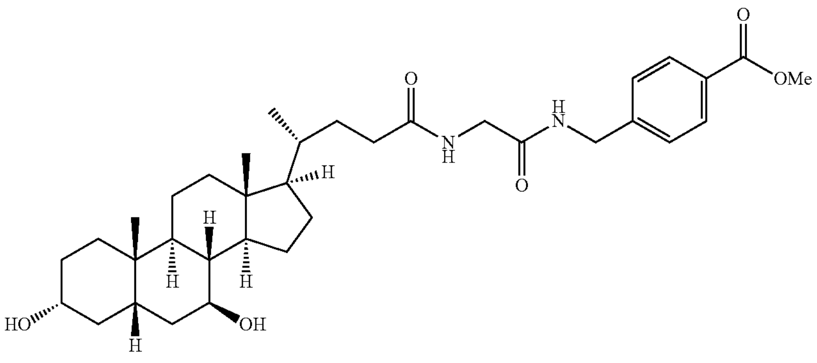

This compound was prepared following method A described above.

Ursodeoxycholic acid (120 mg, 0.27 mmol), methyl 4-(aminomethyl)benzoate hydrochloride (53.8 mg, 0.27), TBTU (104 mg, 0.32 mmol), and $Et_3$ N (0.3 ml 3.26 M). White solid. Yield 63%; Melting point 145-147° C.; IR 3354, 2932, 2861, 1720, 1654, 1281, 1111, 847 $cm^{-1}$; $^1H$ NMR (400 MHz, DMSO-$d_6$) δ 8.41 (t, J=6.1 Hz, 1H), 8.09 (t, J=5.9 Hz, 1H), 7.90 (d, J=8.2 Hz, 2H), 7.38 (d, J=8.1 Hz, 2H), 4.45 (d, J=4.5 Hz, 1H), 4.35 (d, J=6.0 Hz, 2H), 3.87 (d, J=6.8 Hz, 1H), 3.84 (s, 3H), 3.71 (d, J=5.8 Hz, 2H), 3.29 (2H), 2.25-1.96 (m, 2H), 1.95-1.59 (m, 5H), 1.55 -1.25 (m, 9H), 1.25-0.93 (m, 7H), 0.93-0.85 (m, 7H), 0.60 (s, 3H); $^{13}$ C NMR (101 MHz, DMSO-$d_6$) δ 173.14, 169.42, 166.12, 145.21, 129.17, 128.09, 127.31, 69.75, 69.49, 55.89, 54.79, 52.11, 43.11, 43.04, 42.19, 41.78, 38.75, 38.28, 37.76, 37.29, 35.02, 34.86, 33.79, 32.21, 31.46, 30.27, 28.22, 26.76, 23.35, 20.88, 18.53, 12.08. HRMS (ESI) for $C_{28}H_{47}NO_4$, calculated $[[M+H]+[—H_2O]]^+$:579.3798. Obtained: 579.3783.

Example 3: Preparation of methyl((R)-4-((3R,5S,7S,8R,9S,10S,13R,14S,17R)-3,7-dihydroxy-10,13-dimethylhexadecahydro-1H-cyclopenta[a]phenanthren-17-yl)pentanoyl)-L-alaninate

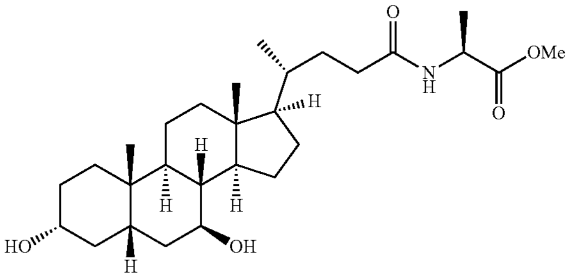

This compound was prepared following method A described above.

Ursodeoxycholic acid (392.6 mg, 1 mmol), L-alanine methyl ester hydrochloride (139.6 mg, 1 mmol), TBTU (385.3 mg, 1.2 mmol), and $Et_3N$ (1.1 ml, 3.26 M). White solid. Yield 45%; Melting point 103-105° C.; IR 3296, 2928, 2863, 1739, 1650, 1209, 1049 $cm^{-1}$; $^1H$ NMR (400 MHz, DMSO-$d_6$) δ 8.19 (d, J=7.0 Hz, 1H), 4.44 (d, J=4.5 Hz, 1H), 4.23 (p, J=7.2 Hz, 1H), 3.87 (d, J=6.8 Hz, 1H), 3.60 (s, 3H), signal corresponding to 2H overlapping the signal of water at 3.29 ppm (confirmed by COSY), 2.19-1.88 (m, 3H), 1.88-1.57 (m, 4H), 1.56-1.27 (m, 9H), 1.27-0.93 (m, 12H), 0.93-0.82 (m, 7H), 0.61 (s, 3H); $^{13}$ C NMR (101 MHz, DMSO-$d_6$) δ 173.26, 172.52, 69.71, 69.45, 55.87, 54.71, 51.72, 47.41, 43.07, 43.01, 42.16, 38.71, 37.72, 37.27, 34.87, 34.82, 33.75, 31.94, 31.47, 30.24, 28.16, 26.71, 23.31, 20.84, 18.47, 16.93, 12.03; HRMS (ESI) for $C_{28}H_{48}NO_5$, calculated $[M+H]^+$: 478.3532. Obtained: 478.3531.

Example 4: Preparation of methyl 3-((R)-4-((3R,5S,7S,8R,9S,10S,13R,14S,17R)-3,7-dihydroxy-10,13-dimethylhexadecahydro-1H-cyclopenta[a]phenanthren-17-yl)pentanamide)propionate

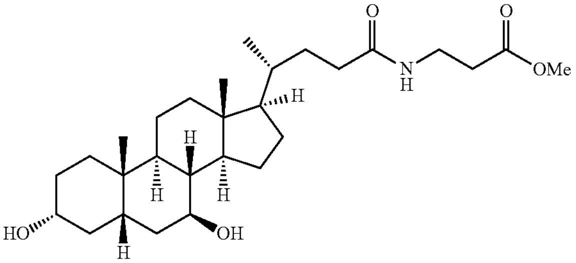

This compound was prepared following method A described above.

Ursodeoxycholic acid (392.6 mg, 1 mmol), β-alanine methyl ester hydrochloride (153.6 mg, 1 mmol), TBTU (385.3 mg, 1.2 mmol), and $Et_3$ N (1.1 ml 3.26 M). White solid. Yield 66%; Melting point 84-86° C.; IR 3292, 2927, 2862, 1734, 1647, 1180, 1049 $cm^{-1}$; $^1H$ NMR (400 MHz, DMSO-$d_6$) δ 7.85 (t, J=5.7 Hz, 1H), 4.43 (d, J=4.6 Hz, 1H), 4.05 (q, J=7.1 Hz, 2H), 3.86 (d, J=6.8 Hz, 1H), 3.29 (2H), 3.24 (q, J=6.5 Hz, 2H), 2.41 (t, J=6.8 Hz, 2H), 2.12-1.89 (m, 4H), 1.89-1.59 (m, 4H), 1.53-1.25 (m, 9H), 1.24-0.90 (m, 11H), 0.87 (t, J=3.3 Hz, 7H), 0.61 (s, 3H); $^{13}$ C NMR (101 MHz, DMSO-$d_6$) δ 172.63, 171.30, 69.70, 69.45, 59.86, 54.69, 43.06, 43.00, 42.16, 38.71, 37.72, 37.26, 34.90, 34.82, 34.65, 33.90, 33.75, 32.29, 31.60, 30.24, 28.15, 26.70, 23.31, 20.84, 18.45, 14.08, 12.01; HRMS (ESI) for $C_{29}H_{50}NO_5$, calculated $[M+H]^+$:492.3689. Obtained: 492.3684.

Example 5: Preparation of methyl ((R)-4-((3R,5S,7S,8R,9S,10S,13R,14S,17R)-3,7-dihydroxy-10,13-dimethylhexadecahydro-1H-cyclopenta[a]phenanthren-17-yl)pentanamide)butanoate

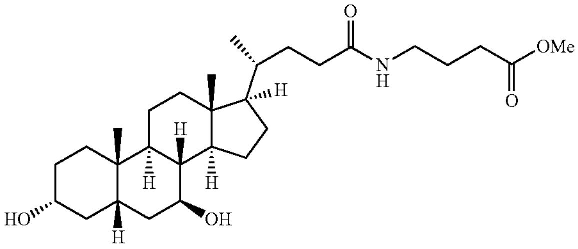

This compound was prepared following method A described above.

Ursodeoxycholic acid (392.6 mg, 1 mmol), 4-aminobutyrate methyl ester hydrochloride (153.6 mg, 1 mmol), TBTU (385.3 mg, 1.2 mmol), and $Et_3$ N (1.1 ml 3.26 M). White solid. Yield 37%; Melting point 92-94° C.; IR 3295, 2927, 2862, 1736, 1646, 1170, 1050 $cm^{-1}$; $^1H$ NMR (400 MHz, DMSO-$d_6$) δ 7.77 (t, J=5.7 Hz, 1H), 4.42 (d, J=4.6 Hz, 1H), 3.85 (d, J=6.8 Hz, 1H), 3.58 (s, 3H), 3.02 (q, J=6.5 Hz, 2H), 2.29 (t, J=7.5 Hz, 2H), 2.15-2.00 (m, 1H), 2.01-1.53 (m, 9H), 1.54-1.24 (m, 8H), 1.24-0.90 (m, 7H), 0.88 (d, J=7.4 Hz, 7H), 0.60 (s, 3H); $^{13}$ C NMR (101 MHz, DMSO- $d_6$) δ 173.04, 172.45, 69.67, 69.41, 55.83, 54.66, 51.20, 43.03, 42.97, 42.13, 38.68, 37.69, 37.60, 37.23, 34.87, 34.79, 33.72, 32.38, 31.63, 30.65, 30.21, 28.14, 26.67, 24.52, 23.28, 18.42, 11.96; HRMS (ESI) for $C_{29}H_{50}NO_5$, calculated $[M+H]^+$:492.3689. Obtained: 492.3686.

Example 6: Preparation of methyl 6-((R)-4-((3R,5S,7S,8R,9S,10S,13R,14S,17R)-3,7-dihydroxy-10,13-dimethylhexadecanohydro-1H-cyclopenta [a] phenanthren-17-yl)pentanamide)hexanoate

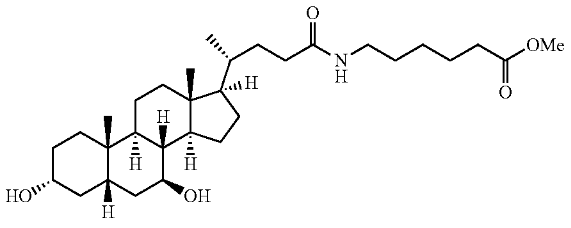

This compound was prepared following method A described above.

Ursodeoxycholic acid (392.6 mg, 1 mmol), 6-aminohexanoate methyl ester hydrochloride (181.7 mg, 1 mmol), TBTU (385.3 mg, 1.2 mmol), and $Et_3$ N (1.1 ml 3.26 M). White solid. Yield 42%; Melting point 78-80° C.; IR 3299, 2926, 2861, 1736, 1644, 1165, 1050 $cm^{-1}$; $^1H$ NMR (400 MHz, DMSO-$d_6$) δ 7.71 (t, J=5.7 Hz, 1H), 4.43 (d, J=4.5 Hz, 1H), 3.86 (d, J=6.7 Hz, 1H), 3.58 (s, 3H), 3.29 (2H), 2.99 (q, J=7.1 Hz, 2H), 2.28 (t, J=7.4 Hz, 2H), 2.14-1.56 (m, 10H), 1.56-0.91 (m, 20H), 0.88 (d, J=7.2 Hz, 8H), 0.60 (s, 3H); $^{13}$ C NMR (101 MHz, DMSO-$d_6$) δ 173.26, 172.28, 69.70, 69.45, 55.87, 54.70, 51.15, 43.06, 43.00, 42.16, 38.71, 38.12, 37.71, 37.26, 34.90, 34.82, 33.75, 33.22, 32.44, 31.69, 30.24, 28.82, 28.16, 26.70, 25.84, 24.15, 23.30, 20.83, 18.45, 12.00; HRMS (ESI) for $C_{31}H_{54}NO_5$, calculated $[M+H]^+$:520.4002. Obtained: 520.3997.

Example 7: Preparation of methyl 5-(((R)-4-((3R,5S,7S,8R,9S,105,13R,14S,17R)-3,7-dihydroxy-10,13-dimethylhexadecanohydro-1H-cyclopenta[a] phenanthren-17-yl)pentanamide)methyl)furan-2-carboxylate

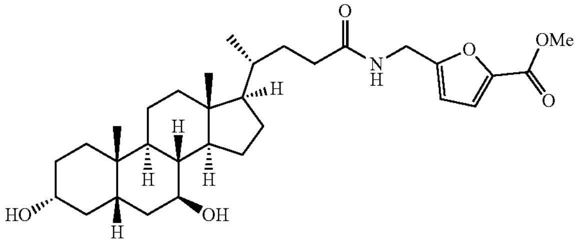

This compound was prepared following method A described above.

Ursodeoxycholic acid (145 mg, 0.37 mmol), 5-(aminomethyl)furan-2-carboxylate methyl ester hydrochloride (70.9 mg, 0.37), TBTU (146.4 mg, 0.46 mmol), and $Et_3$ N (0.41 ml 3.26 M). White solid. Yield 52%; Melting point 240-242° C.; IR 3463, 3285, 2935, 1705, 1683, 1518, 1210, 763 $cm^{-1}$; $^1H$ NMR (400 MHz, DMSO-$d_6$) δ 8.38 (t, J=5.8 Hz, 1H), 7.23 (d, J=3.5 Hz, 1H), 6.40 (d, J=3.4 Hz, 1H), 4.42 (d, J=4.5 Hz, 1H), 4.29 (d, J=5.7 Hz, 2H), 3.85 (d, J=6.8 Hz, 1H), 3.79 (s, 3H), signal corresponding to 2H overlapping the signal of water at 3.29 ppm (confirmed by COSY), 2.09 (m, J=39.5, 14.2, 7.9 Hz, 2H), 1.96-1.58 (m, 5H), 1.54-1.24 (m, 10H), 1.24-0.90 (m, 8H), 0.87 (d, J=6.5 Hz, 7H), 0.58 (s, 3H); $^{13}$ C NMR (101 MHz, DMSO-$d_6$) δ 172.63, 158.23, 157.68, 142.62, 119.31, 109.11, 69.71, 69.45, 55.85, 54.69, 51.65, 43.06, 43.00, 42.16, 39.99, 38.71, 37.72, 37.27, 35.57, 34.86, 34.82, 33.75, 32.20, 31.54, 30.24, 28.15, 26.70, 23.30, 18.42, 11.99; HRMS (ESI) for $C_{31}H_{51}N_2O_6$, calculated $[M+NH_4]^+$: 547.3745. Obtained: 547.3738.

Example 8: Preparation of 4-(((R)-4-((3R,5S,7S,8R,9S,10S,13R,14S,17R)-3,7-dihydroxy-10,13-dimethylhexadecanohydro-1H-cyclopenta[a]phenanthren-17-yl)pentanamide)methyl)benzoic acid

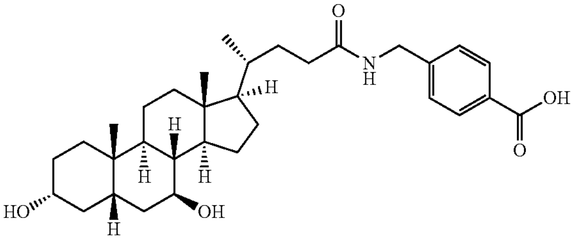

This compound was prepared following the processes described in method B. Methyl 4-(((R)-4-((3R,5S,7S,8R,9S,10S,13R,14S,17R)-3,7-dihydroxy-10,13-dimethylhexadecahydro-1H-cyclopenta[a]phenanthren-17-yl)pentanamide)methyl)benzoate (1079 mg, 2 mmol) and NaOH (8.7 ml 0.5M). Yield 90%; Melting point 155-157° C.; IR 3288, 2922, 2851, 1638, 1542, 1281, 1015 $cm^{-1}$; $^1H$ NMR (400 MHz, DMSO-$d_6$) δ 12.85 (s, 1H), 8.37 (t, J=6.0 Hz, 1H), 7.88 (d, J=8.2 Hz, 2H), 7.34 (d, J=8.1 Hz, 2H), 4.48-4.39 (m, 1H), 4.34-4.28 (m, 2H), 3.86 (d, J=6.8 Hz, 1H), 3.29 (2H) (confirmed by COSY), 2.24-2.01 (m, 2H), 1.98-1.60 (m, 6H), 1.53-1.26 (m, 10H), 1.26-0.93 (m, 7H), 0.93-0.85 (m, 7H), (s, 3H); $^{13}$ C NMR (101 MHz, DMSO-$d_6$) δ 172.67, 167.15, 145.01, 129.30, 129.19, 127.10, 69.73, 69.47, 55.88, 54.76, 43.09, 43.01, 42.18, 41.77, 39.84, 38.74, 37.73, 37.27, 34.89, 34.83, 33.76, 32.38, 31.65, 30.25, 28.19, 26.72, 23.32, 20.85, 18.44, 12.01; HRMS (ESI) for $C_{32}H_{48}NO_5$, calculated $[M+H]^+$: 525.3532. Obtained: 525.3538.

Example 9: Preparation of methyl ((4-(((R)-4-((3R, 5S,7S,8R,9S,10S,13R,14S,17R)-3,7-dihydroxy-10, 13-dimethylhexadecahydro-1H-cyclopenta [a] phenanthren-17-yl)pentanamide)methyl) benzamido) methyl)benzoate

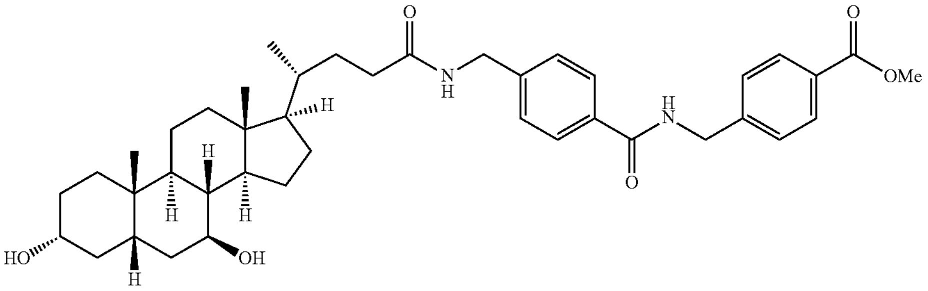

This compound was prepared following the processes described in method A. 4-(((4R)-4-((3R,5S,7S,8R,9S,10S, 13R,145-3,7-dihydroxy-10,13-dimethylhexadecanohydro-1H-cyclopenta[a]phenanthren-17-yl)pentanamide)methyl) benzoic acid (200 mg, 0.38 mmol), methyl 4-(aminomethyl) benzoate hydrochloride (76.6 mg 0.38 mmol), TBTU (146.4 mg 0.46 mmol), and $Et_3$ N (0.42 ml 3.26 M). White solid. Yield 60%; Melting point 139-141° C.; IR 3301, 2926, 2861, 1719, 1638, 1276, 1107, 1047 $cm^{-1}$; $^1$H NMR (400 MHz, DMSO-$d_6$) δ 9.08 (t, J=6.0 Hz, 1H), 8.36 (t, J=6.0 Hz, 1H), 7.92 (d, J=8.1 Hz, 2H), 7.85 (d, J=8.1 Hz, 2H), 7.44 (d, J=8.1 Hz, 2H), 7.32 (d, J=8.1 Hz, 2H), 4.55 (d, J=5.9 Hz, 2H), 4.45 (d, J=4.5 Hz, 1H), 4.36-4.15 (m, 2H), 3.87 (d, J=6.8 Hz, 1H), 3.83 (s, 3H), 3.29 (2H), 2.23-2.01 (m, 2H), 1.97-1.59 (m, 6H), 1.55-1.25 (m, 10H), 1.25-0.93 (m, 7H), 0.93-0.82 (m, 7H), 0.61 (s, 3H); $^{13}$ C NMR (101 MHz, DMSO-$d_6$) 6 172.67, 166.11, 145.41, 143.37, 132.52, 129.25, 128.10, 127.29, 126.95, 69.73, 69.48, 55.88, 54.77, 52.06, 43.10, 43.02, 42.40, 42.18, 41.71, 38.73, 37.73, 37.28, 34.91, 34.84, 33.77, 32.41, 31.68, 28.20, 26.73, 23.32, 20.86, 18.46, 12.04; HRMS (ESI) for $C_{41}H_{57}N_2O_6$, calculated $[M+H]^+$:673. Obtained: 673.4214.

Example 10 (Synthesis Ia): Preparation of 4-((2-((R) -4-((3R, 5S, 7S, 8R, 9S, 10S, 13R, 14S, 17R) -3,7-dihydroxy-10,13-dimethylhexadecahydro-1H-cyclopenta [a]phenanthren-17-yl)pentanamide) acetamido)methyl)-N-hydroxybenzamide

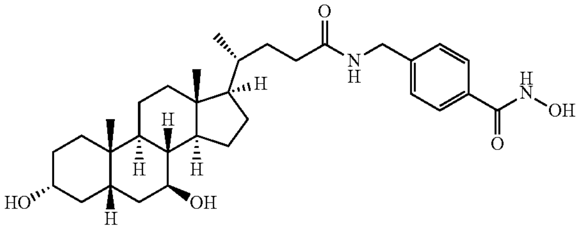

This compound was prepared following method C described above.

A suspension of sodium methoxide in methanol (previously prepared 2.0 g, 37 mmol solution) was added dropwise to a solution containing hydroxylamine hydrochloride (694.9 mg, 10 mmol) and phenolphthalein (1 mg) under inert atmosphere and at until a permanent color change from white to pink was observed. Next, methyl 4-(((R)-4-((3R, 5S,7S,8R,9S,10S,13R,14S,17R)-3,7-dihydroxy-10,13-dimethylhexadecahydro-1H-cyclopenta[a]phenanthren-17-yl) pentanamide)methyl)benzoate (539.4 mg, 1 mmol) dissolved in dry methanol (1 ml) was added. The reaction mixture was left to reach room temperature, and its progression was monitored by thin layer chromatography. The initial reagents were consumed after 90 hours. After this time has lapsed, distilled water (10 ml) and the reaction medium were added, and it was acidified with glacial acetic acid. The product was then extracted with diethyl ether (3×20 ml). The combined organic fractions were dried on $MgSO_4$ and evaporated under reduced pressure. The product thus obtained was dissolved again in methanol (1 ml) and precipitated with water. This precipitate was filtered and the solvent was evaporated. The title product was thereby obtained as a white solid. Yield 61%; Melting point 170-172° C.; IR 3275, 2927, 2862, 1638, 1535, 1012 $cm^{-1}$; $^1$H NMR (400 MHz, DMSO-$d_6$) δ 11.17 (s, 1H), 9.01 (s, 1H), 8.34 (t, J=6.0 Hz, 1H), 7.69 (d, J=8.1 Hz, 2H), 7.29 (d, J=8.1 Hz, 2H), 4.44 (d, J=4.5 Hz, 1H), 4.28 (dd, J=5.9, 3.6 Hz, 2H), 3.87 (d, J=6.8 Hz, 1H), 3.29 (2H). 2.24-2.01 (m, 2H), 1.99-1.59 (m, 6H), 1.56-1.26 (m, 10H), 1.26-0.94 (m, 7H), 0.94-0.84 (m, 7H), 0.62 (s, 3H); $^{13}$ C NMR (101 MHz, DMSO-$d_6$) δ 172.63, 163.99, 143.06, 131.18, 126.92, 126.83, 69.73, 69.47, 54.76, 43.09, 43.02, 42.18, 41.71, 39.85, 38.73, 37.73, 37.27, 34.93, 34.84, 33.77, 32.38, 31.67, 30.25, 28.21, 26.73, 23.33, 20.86, 18.44, 12.04; HRMS (ESI) for $C_{32}H_{47}N_2O_4$, calculated $[[M+H]+[-H_2O]]^+$:523.3536. Obtained: 523.3536.

Example 11 (Synthesis Ib) : Preparation of 4-((2-((R)-4((3R, 5S, 7S, 8R, 9S, 10S, 13R, 14S, 17R) -3,7-dihydroxy-10,13-dimethylhexadecahydro-1H-cyclopenta [a] phenanthren-17-yl)pentanamide)acetamido)methyl)-N-hydroxybenzamide

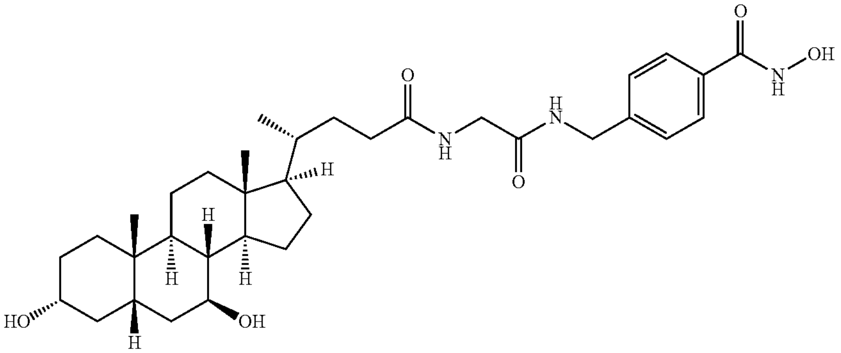

This compound was prepared following method C described above.

4-((2-((R)-4-((3R,5S,7S,8R,9S,10S,13R,145,17R)-3,7-dihydroxy-10,13-dimethylhexadecahydro-1H-cyclopenta[a] phenanthren-17-yl)pentanamide)acetamido)methyl)benzoate (83.9 mg, 0.14 mmol), hydroxylamine hydrochloride (97.3 mg, 1.4 mmol), phenolphthalein (1 mg), and sodium methoxide (previously prepared 2.0 mg, 37 mmol solution). White solid. Yield 42%; Melting point 153-155° C.; IR 3217, 2928, 2864, 1641, 1534, 1013 $cm^{-1}$; $^{1}H$ NMR (400 MHz, DMSO-$d_6$) δ 11.17 (s, 1H), 8.98 (s, 1H), 8.35 (t, J=6.0 Hz, 1H), 8.05 (t, J=5.9 Hz, 1H), 7.69 (d, J=8.1 Hz, 2H), 7.30 (d, J=8.0 Hz, 2H), 4.46-4.40 (m, 1H), 4.31 (d, J=6.0 Hz, 2H), 3.86 (d, J=6.7 Hz, 1H), 3.71 (d, J=5.9 Hz, 2H), 3.29 (2H) , 2.11 (m, J=57.0, 14.2, 10.0, 5.6 Hz, 2H), 1.97-1.89 (m, 1H), 1.90-1.58 (m, 5H), 1.54-1.25 (m, 10H), 1.25-0.93 (m, 7H), 0.93-0.83 (m, 7H), 0.61 (s, 3H); $^{13}$ C NMR (101 MHz, DMSO-$d_6$) δ 173.04, 169.24, 164.03, 142.70, 131.21, 126.94, 126.81, 69.71, 69.46, 54.73, 43.07, 43.01, 42.17, 42.10, 41.71, 38.72, 37.72, 37.27, 34.98, 34.83, 33.76, 32.18, 31.42, 30.25, 28.18, 26.72, 23.31, 20.85, 18.51, 12.05; HRMS (ESI) for $C_{34}H_{52}N_3O_6$, calculated $[M+H]^+$: 598.3856. Obtained: 598.3857.

Example 12 (Synthesis Ic): Preparation of (R)-4-((3R,5S,7S,8R,9S,10S,13R,14S,17R)-3,7-dihydroxy-10,13-dimethylhexadecanohydro-1H-cyclopenta [a] phenanthren-17-yl) -N-((S)-1-(hydroxy-amino)-1-aminopropan-2-yl)pentanamide

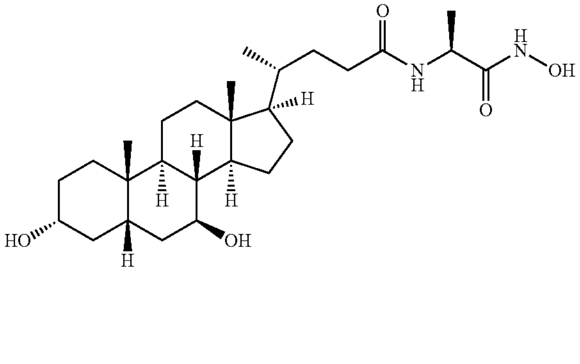

This compound was prepared following the processes described in method C.

Methyl ((R)-4-((3R,5S,7S,8R,9S,10S,13R,14S,17R)-3,7-dihydroxy-10,13-dimethylhexadecahydro-1H-cyclopenta[a] phenanthren-17-yl)pentanoyl)-L-alaninate, hydroxylamine hydrochloride (278 mg, 4 mmol), phenolphthalein (1 mg), and sodium methoxide (2.0 g, 37 mmol). The compound was isolated as a white solid. Yield 22%; Melting point 170-172° C.; IR 3265, 2928, 2863, 1642, 1537, 1047 $cm^{-1}$; $^{1}H$ NMR (400 MHz, DMSO-$d_6$) δ 7.96 (d, J=7.8 Hz, 1H), 4.44 (s, 1H), 4.17 (p, J=7.1 Hz, 1H), 3.86 (d, J=6.6 Hz, 1H),3.29 (2H)), 2.13 (m, J=14.8, 5.2 Hz, 1H), 2.04-1.89 (m, 2H), 1.89-1.55 (m, 4H), 1.54-1.24 (m, 10H), 1.22-0.93 (m, 11H), 0.88 (d, J=6.1 Hz, 7H), 0.61 (s, 3H); $^{13}$ C NMR (101 MHz, DMSO-$d_6$) δ 172.19, 169.09, 69.71, 69.45, 55.87, 54.71, 45.74, 43.07, 43.01, 42.16, 38.72, 37.72, 37.26, 35.03, 34.83, 33.75, 32.10, 31.48, 30.24, 28.18, 26.72, 23.31, 20.84, 18.49, 12.04. HRMS (ESI) for $C_{27}H_{47}N_2O_5$, calculated $[M+H]^+$: 479.3485. Obtained: 479.3483.

Example 13 (Synthesis Id): Preparation of (4R)-4-((3R, 5S, 7S, 8R, 9S, 10S, 13R, 14S) -3,7-dihydroxy-10,13-dimethylhexadecane-1H-cyclopenta [a]phenanthren-17-yl)-N-(3-(hydroxyamino)-3-oxopropyl)pentanamide

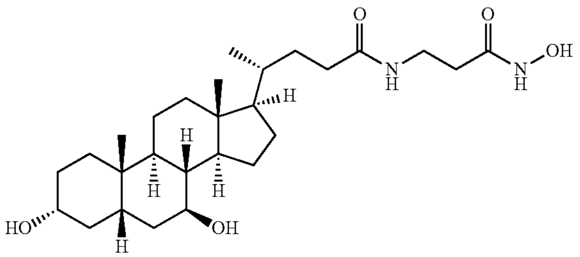

This compound was prepared following the processes described above in method C.

Methyl 3-((R)-4-((3R,5S,7S,8R,9S,10S,13R,14S,17R)-3,7-dihydroxy-10,13-dimethylhexadecahydro-1H-cyclopenta [a]phenanthren-17-yl)pentanamide)propionate (298 mg, 0.61 mmol), hydroxylamine hydrochloride (424.5 mg, 6.1 mmol), phenolphthalein (1 mg), and sodium methoxide (2.0 g, 37 mmol). The product was obtained as a white solid. Yield 59%; Melting point 180-182° C.;

IR 3271, 2927, 2862, 1638, 1542, 1047 $cm^{-1}$; $^{1}H$ NMR (400 MHz, DMSO-$d_6$) δ 7.82 (t, J=5.7 Hz, 1H), 4.43 (s, 1H), 3.86

(d, J=6.8 Hz, 1H), 3.30 (s, 2H), 3.19 (q, J=6.8 Hz, 2H), 2.11 (m, 2H), 1.99-1.56 (m, 8H), 1.54-1.24 (m, 8H), 1.23-0.90 (m, 9H), (d, J=4.4 Hz, 7H), 0.61 (s, 3H); $^{13}$C NMR (101 MHz, DMSO-$d_6$) δ 172.53, 167.03, 69.71, 69.45, 55.86, 54.70, 43.07, 43.01, 42.16, 39.99, 38.71, 37.72, 37.27, 35.27, 34.98, 34.83, 33.75, 32.53, 32.35, 31.59, 30.24, 28.17, 26.71, 23.31, 20.84, 18.47, 12.04; HRMS (ESI) for $C_{27}H_{47}N_2O_5$, calculated [M +H]$^+$:479.3485. Obtained: 479.3480.

Example 14 (Synthesis Ie): Preparation of (R)-4-((3R,5S,7S,8R,9S,10S,13R,14S,17R)-3,7-dihydroxy-10,13-dimethylhexadecahydro-1H-cyclopenta[a]phenanthren-17-yl)-N-(4-(hydroxyamino)-4-oxobutyl)pentanamide

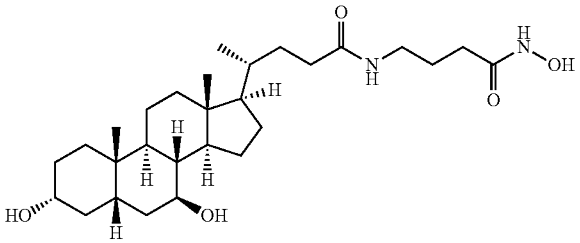

This compound was prepared following the processes described in method C.

Methyl ((R)-4-((3R,5S,7S,8R,9S,10S,13R,14S,17R)-3,7-dihydroxy-10,13-dimethylhexadecahydro-1H-cyclopenta[a]phenanthren-17-yl)pentanamide)butanoate (165 mg, mmol), hydroxylamine hydrochloride (236.6 mg, 3.4 mmol), phenolphthalein (1 mg), and sodium methoxide (previously prepared 2.0 mg, 37 mmol solution). The compound was isolated as a white solid. Yield 54%; Melting point 165-167° C.; IR 3269, 2928, 2862, 1643, 1550, 1047 cm$^{-1}$; $^1$H NMR (400 MHz, DMSO-$d_6$) δ 7.81 (t, J=Hz, 1H), 4.46 (s, 1H), 3.88 (d, J=6.6 Hz, 1H), signal corresponding to 2H overlapping the signal of water at 3.29 ppm (confirmed by COSY), 3.00 (q, J=6.6 Hz, 2H), 2.16-1.91 (m, 6H), 1.89-1.54 (m, 7H), 1.54-1.25 (m, 9H), 1.25-0.92 (m, 9H), 0.89 (d, J=7.8 Hz, 7H), 0.62 (s, 3H); $^{13}$C NMR (101 MHz, DMSO-$d_6$) δ 172.45, 168.69, 69.71, 69.45, 55.87, 54.70, 43.07, 43.01, 42.17, 38.72, 38.05, 37.72, 37.27, 34.97, 34.83, 33.76, 32.43, 31.67, 30.24, 29.91, 28.18, 26.72, 25.45, 23.31, 20.84, 18.48, 12.03; HRMS (ESI) for $C_{28}H_{49}N_2O_5$, calculated [M+H]$^+$:493.3641. Obtained: 493.3642.

Example 15 (Synthesis If): Preparation of 6-((R)-4-((3R,5S,7S,8R,9S,10S,13R,14S,17R)-3,7-dihydroxy-10,13-dimethylhexadecahydro-1H-cyclopenta[a]phenanthren-17-yl)pentanamide)-N-hydroxyhexanamide

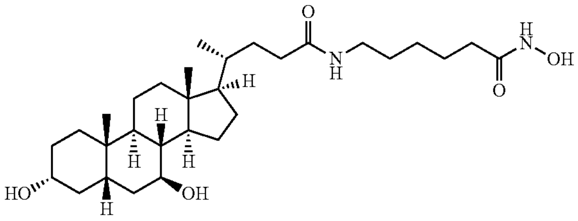

This compound was prepared following the process described in method C.

Methyl 6-((R)-4-((3R,5S,7S,8R,9S,10S,13R,14S,17R)-3,7-dihydroxy-10,13-dimethylhexadecanohydro-1H-cyclopenta[a]phenanthren-17-yl)pentanamide)hexanoate (200 mg, mmol), hydroxylamine hydrochloride (262.9, 3.8 mmol), phenolphthalein (1 mg), and sodium methoxide (previously prepared 2.0 mg, 37 mmol solution). The compound was isolated as a white solid. Yield 43%; Melting point 125-127° C.; IR 3269, 2927, 2861, 1642, 1547, 1047 cm$^{-1}$; $^1$H NMR (400 MHz, DMSO-$d_6$) δ 10.32 (s, 1H), 8.64 (s, 1H), 7.71 (t, J=5.6 Hz, 1H), 4.43 (d, J=4.5 Hz, 1H), 3.86 (d, J=6.8 Hz, 1H), 3.29 (2H)), 2.98 (q, J=6.5 Hz, 2H), 2.06 (m, J=14.5, 9.7, 5.2 Hz, 1H), 2.00-1.53 (m, 9H), 1.55-1.26 (m, 14H), 1.26-0.90 (m, 9H), 0.88 (d, J=7.3 Hz, 7H), 0.61 (s, 3H); $^{13}$C NMR (101 MHz, DMSO-$d_6$) δ 172.28, 168.99, 69.71, 69.45, 55.87, 54.70, 43.07, 43.00, 42.16, 38.72, 38.27, 37.72, 37.26, 34.93, 34.82, 33.75, 32.43, 32.20, 31.69, 30.24, 28.93, 28.18, 26.71, 26.04, 24.88, 23.31, 20.84, 18.47, 12.02; HRMS (ESI) for $_{30}H_{53}N_2O_5$, calculated [M+H]$^+$: 521.3954. Obtained: 521.3955.

Example 16 (Synthesis Ig): Preparation of 4-(((R)-4-((3R,5S,7S,8R,9S,10S,13R,14S,17R)-3,7-dihydroxy-10,13-dimethylhexadecanohydro-1H-cyclopenta [a]phenanthren-17-yl) pentanamido)methyl)-N-(4-(hydroxycarbamoyl)benzyl)benzamide

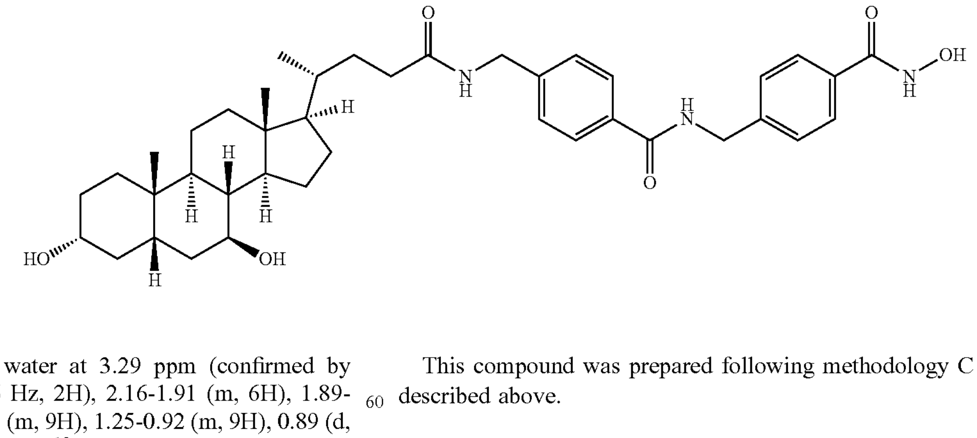

This compound was prepared following methodology C described above.

Methyl ((4-(((R)-4-((3R,5S,7S,8R,9S,10S,13R,14S,17R)-3,7-dihydroxy-10,13-dimethylhexadecahydro-1H-cyclopenta[a]phenanthren-17-yl)pentanamide)methyl)benzamido)methyl)benzoate (133.7 mg, 0.2 mmol), hydroxylamine hydrochloride (139.2, 2 mmol), phenolphthalein (1 mg), and sodium methoxide (previously prepared 2.0 mg, 37 mmol solution). The compound was isolated as a white solid. Yield 60%; Melting point 187-189° C.; IR 3288, 2922, 2851, 1638, 1542, 1015 $cm^{-1}$; $^1H$ NMR (400 MHz, DMSO-$d_6$) δ 9.03 (t, J=6.0 Hz, 1H), 8.35 (t, J=6.0 Hz, 1H), 7.84 (d, J=8.0 Hz, 2H), 7.70 (d, J=7.9 Hz, 2H), 7.33 (dd, J=8.0 Hz, 4H), 4.50 (d, J=5.9 Hz, 2H), 4.46-4.40 (m, 1H), 4.36-4.22 (m, 2H), 3.88 (s, 1H), 3.92 (2H) , 2.28-1.99 (m, 2H), 1.99-1.56 (m, 5H), 1.54-1.25 (m, 9H), 1.25-0.94 (m, 8H), 0.94-0.84 (m, 8H), 0.61 (s, 3H); $^{13}$ C NMR (101 MHz, DMSO-$d_6$) δ 172.63, 166.03, 164.08, 143.29, 142.96, 132.60, 131.26, 127.24, 126.99, 126.90, 69.71, 69.46, 55.86, 54.74, 43.08, 43.01, 42.35, 42.16, 41.69, 39.99, 38.71, 37.71, 37.27, 34.91, 34.82, 33.76, 32.38, 31.66, 30.24, 28.18, 26.72, 23.31, 20.84, 18.45, 12.03; HRMS (ESI) for $C_{40}H_{54}N_3O_5$, calculated $[[M+H]+[—H_2O]]^+$:656.4064.

Obtained: 656.4054.

Example 17 (Synthesis Ih): Preparation of 5-(((R)-4-((3R,5S,7S,8R,9S,10S,13R,14S,17R)-3,7-dihydroxy-10,13-dimethylhexadecahydro-1H-cyclopenta[a]phenanthren-17-yl) pentanamido)methyl)-N-hydroxyfuran-2-carboxamide

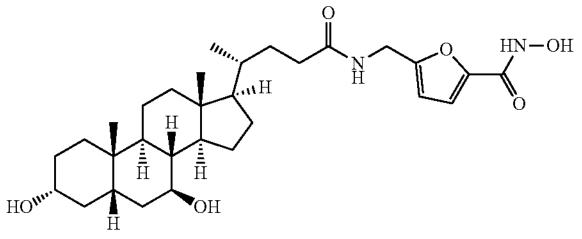

This compound was prepared following methodology C described above.

Methyl 5-(((R)-4-((3R,5S,7S,8R,9S,10S,13R,145,17R)-3,7-dihydroxy-10,13-dimethylhexadecanohydro-1H-cyclopenta[a]phenanthren-17-yl)pentanamide)methyl)furan-2-carboxylate (79.4 mg, 0.15 mmol), hydroxylamine hydrochloride (104.4, 1.5 mmol), phenolphthalein (1 mg), and sodium methoxide (previously prepared 2.0 mg, 37 mmol solution). The compound was isolated as a white solid. Yield 47%; Melting point 149-151° C.; IR 3272, 2929, 2864, 1644, 1540, 1016 $cm^{-11}$H NMR (400 MHz, DMSO-$d_6$) δ 11.02 (s, 1H), 9.05 (s, 1H), 8.30 (t, J=5.6 Hz, 1H), 6.95 (d, J=3.3 Hz, 1H), 6.30 (d, J=3.4 Hz, 1H), 4.43 (d, J=4.6 Hz, 1H), 4.26 (d, J=5.5 Hz, 2H), 3.86 (d, J=6.8 Hz, 1H), 3.26 (d, J=5.2 Hz, OH), 2.24-1.97 (m, 2H), 1.97-1.56 (m, 6H), 1.56-1.25 (m, 9H), 1.25-0.93 (m, 7H), 0.93-0.83 (m, 8H), (s, 3H).; $^{13}$ C NMR (101 MHz, DMSO-$d_6$) δ 172.57, 156.39, 154.91, 144.99, 113.56, 108.14, 69.71, 69.45, 55.86, 54.69, 43.07, 43.01, 42.16, 38.71, 37.72, 37.27, 35.62, 34.93, 34.83, 33.76, 32.18, 31.52, 30.24, 28.16, 26.71, 23.31, 20.84, 18.45, 12.03; HRMS (ESI) for $C_{30}H_{45}N_2O_5$, calculated $[[M+H]+[—H_2O]]^+$: 513.3329. Obtained: 513.3327.

Example 18 (Synthesis Ii): Preparation of N-(2-aminophenyl)-4-(((R)-4-((3R,5S,7S,8R,9S,10S,13R,14S,17R)-3,7-dihydroxy-10,13-dimethylhexadecahydro-1H-cyclopenta[a]phenanthren-17-yl) pentanamide)methyl)benzamide

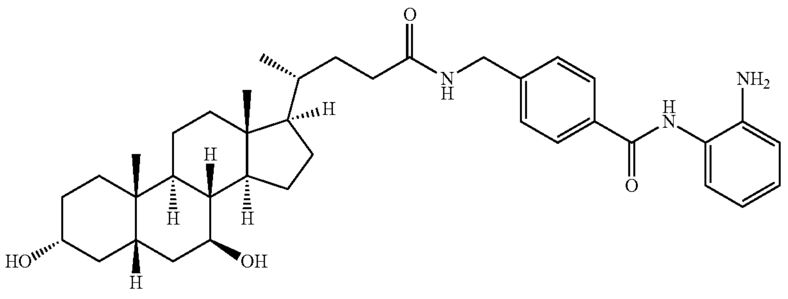

This compound was prepared following method A described above.

4-(((R)-4-((3R,5S,7S,8R,9S,10S,13R,14S,17R)-3,7-dihydroxy-10,13-dimethylhexadecanohydro-1H-cyclopenta[a] phenanthren-17-yl)pentanamide)methyl)benzoic acid (200 mg, 0.38 mmol), o-phenylenediamine (41.1 mg 0.38 mmol), TBTU (146.4 mg 0.46 mmol), and $Et_3$ N (0.42 ml 3.26 M). The compound was isolated as a white solid. Yield 39%; Melting point 168-170° C.; IR 3294, 2927, 2862, 1647, 1505, 1048, 745 $cm^{-1}$; $^1H$ NMR (400 MHz, DMSO-$d_6$) δ 9.61 (s, 1H), 8.38 (t, J=6.0 Hz, 1H), 7.92 (d, J=7.9 Hz, 2H), 7.35 (d, J=7.9 Hz, 2H), 7.16 (d, J=7.9 Hz, 1H), 7.04-6.92 (m, 1H), 6.78 (dd, J=8.0, 1.4 Hz, 1H), 6.69-6.49 (m, 1H), 4.88 (s, 2H), 4.42 (d, J=4.6 Hz, 1H), 4.37-4.25 (m, 2H), 3.86 (d, J=6.8 Hz, 1H), 3.29 (2H), 2.25-2.01 (m, 2H), 1.98-1.58 (m, 6H), 1.56-1.27 (m, 9H), 1.27-0.94 (m, 5H), 0.94-0.82 (m, 10H), 0.62 (s, 3H); $^{13}$ C NMR (101 MHz, DMSO-d) δ 172.63, 165.05, 143.38, 143.11, 132.99, 127.74, 126.81, 126.66, 126.43, 123.32, 116.23, 116.11, 69.70, 69.46, 55.87, 54.75, 43.08, 43.01, 42.15, 41.71, 38.71, 37.71, 37.26, 34.91, 34.82, 33.75, 32.39, 31.69, 30.24, 28.19, 26.72, 23.31, 20.84, 18.45, 12.03; HRMS (ESI) for $C_{38}H_{54}$ $N_3O_4$, calculated $[M+H]^+$:616.4114.

Obtained: 616.4110.

Example 19 (Synthesis Ij): Preparation of N-(4-amino-[1,1'-biphenyl]-3-yl)-4-(((R)-4-((3R,5S,7S,8R,9S,10S,13R,14S,17R)-3,7-dihydroxy-10,13-dimethylhexadecahydro-1H-cyclopenta[a]phenanthren-17-yl)pentanamide)methyl)benzamide

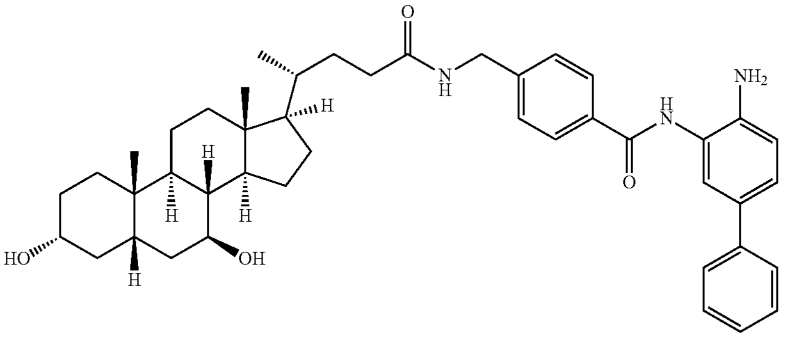

Process for preparing tert-butyl (3-amino-[1,1'-biphenyl]-4-yl)carbamate

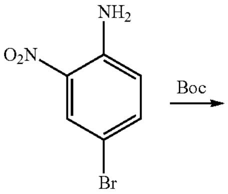

A

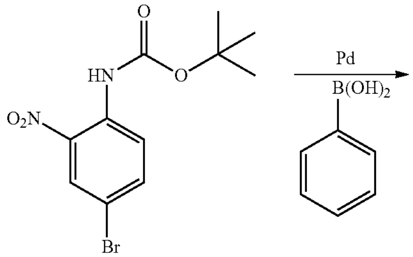

B

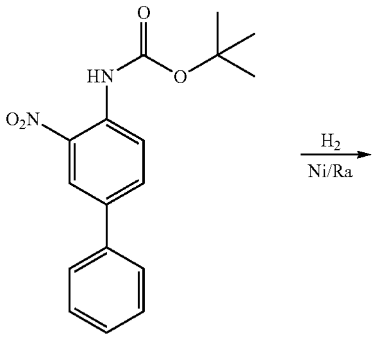

C

-continued

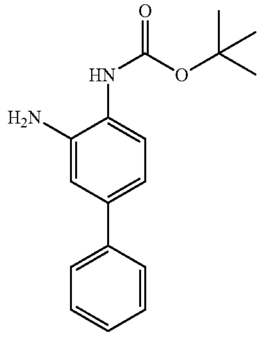

D

The synthesis of Cert-butyl (3-amino-[1,1'-biphenyl]-4-yl)carbamate is described below.

A catalytic amount of DMAP (4-dimethylamino pyridine) was added to a solution of 4-bromo-2-nitroaniline (A) (2.4 g, 11.05 mmol) and Boc-anhydride (di-cert-butyl dicarbonate) (5.08 ml, 22.11 mmol) in THF (20 ml). The reaction was kept under stirring for 90 minutes at room temperature. The solvent was then evaporated at low pressure and the oil obtained was dissolved in THF (10 ml). Next, NaOH (10 ml of a 2N solution) was added and the reaction was kept under stirring for 18 hours at 65° C. After this time has lapsed, NaOH (10 mmol) was added and the reaction was kept under stirring for an additional 4 hours at 65° C. The progression of the reaction was followed by thin layer chromatography. The solvent was removed under vacuum, giving rise to a solid residue, which was filtered and washed with distilled water (2x20 ml), the desired product being obtained as a yellow solid, which was used directly in the next reaction step to obtain C.

$Pd(PPh_3)_4$ (10%, 0.346 mmol) was added to a reaction mixture in DME/$H_2O$ (2:1, 5 ml) containing the corresponding previously obtained Cert-butyl carbamate (1 g, 3.15 mmol), phenylboronic acid (422.91 mg 3.46 mmol), and sodium carbonate (491.8 mg, 4.73 mmol), and it was kept under stirring for 20 hours at 110° C. and an inert atmosphere. After this reaction time has lapsed, water was added and the product was extracted with ethyl acetate (3x20 ml). The organic phases were pooled and washed with water (2×10 ml), the solvent was dried on magnesium sulfate, filtered, and evaporated at reduced pressure. The yellow solid thus obtained was purified by means of chromatography, the desired product C being obtained. The last step of the reaction which consists of reducing the $NO_2$ group to $NH_2$ was carried out using a modular catalytic hydrogenator (H-Cube Pro by ThalesNano) and a CatCart or a catalyst cartridge system, which in this case contains Ni/Ra supported thereon. To carry out the reaction, compound (X) was dissolved in 500 ml of MeOH and passed through the catalytic system at a flow rate of 1 ml/min, at 50° C., and a pressure of 10 bars. The solvent was removed under vacuum giving rise to a white solid which corresponds with the desired product D. Once the reaction has ended, the BOC protecting group was released using acidic conditions (HCl, TFA, etc) to that end to give rise to the desired compound as a white solid.

Yield 22%; Melting point 163-165° C.;

IR 3321, 2927, 2862, 1649, 1489, 1048, 760, 698 cm-1; $^1$H NMR (400 MHz, DMSO-$d_6$) δ 9.70 (s, 1H), 8.39 (t, J=6.0 Hz, 1H), 7.95 (d, J=7.9 Hz, 2H), 7.59-7.49 (m, 3H), 7.45-7.29 (m, 5H), 7.25 (q, J=7.3, 6.6 Hz, 1H), 6.87 (d, J=8.3 Hz, 1H), 5.08 (s, 2H), 4.43 (d, J=4.6 Hz, 1H), 4.33 (dd, J=5.9, 3.8 Hz, 2H), 3.86 (d, J=6.8 Hz, 1H), signal corresponding to 2H overlapping the signal of water at 3.29 ppm (confirmed by COSY), 2.29-1.88 (m, 3H), 1.89-1.59 (m, 6H), 1.54-1.26 (m, 10H), 1.26-0.97 (m, 4H), 0.97-0.83 (m, 9H), 0.62 (s, 3H); $^{13}$ C NMR (101 MHz, DMSO-$d_6$) δ 172.66, 165.23, 143.46, 142.74, 140.17, 132.98, 128.78, 128.13, 127.81, 126.83, 126.00, 125.49, 124.75, 124.65, 123.60, 116.52, 69.71, 69.46, 55.88, 54.75, 43.09, 43.01, 42.16, 41.73, 38.72, 37.72, 37.27, 34.93, 34.83, 33.76, 32.41, 31.70, 30.24, 28.20, 26.73, 23.31, 20.85, 18.46, 12.04; HRMS (ESI) for $C_{44}H_{58}N_3O_4$, calculated [M+H]+:692.4427. Obtained: 692.4414.

Example 20 (Synthesis Ik): Preparation of (R)-4-((3R,5S,7S,8R,9S,10S,13R,14S,17R)-3,7-dihydroxy-10,13-dimethylhexadecanohydro-1H-cyclopenta [a] phenanthren-17-yl)-N-(2-mercaptoethyl)pentanamide

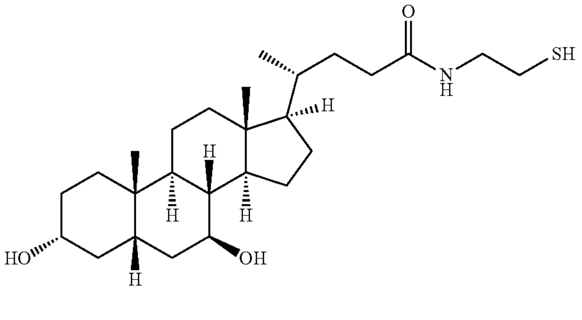

This compound was prepared following method A described above.

Ursodeoxycholic acid (250 mg, 0.63 mmol) with 2-(tritylthio)ethan-1-amine hydrochloride (202.3 mg, 0.63 mmol). To release the trityl group, trifluoroacetic acid (0.60 ml, and triethylsilane (0.20 ml) were added, and the resulting mixture was stirred at room temperature for 2 hours. After these two hours, $NaHCO_3$ (7.7 ml, saturated aqueous solution) was added and the resulting mixture was stirred for 60 minutes. The organic phase was separated and the aqueous layer was extracted with $CH_2Cl_2$ (3×15 ml). The organic fractions were combined and dried on $Na_2SO_4$, the solvent was filtered and removed at reduced pressure to obtain 103 mg of the desired product as a white solid. Yield 36%; Melting point 116-117° C.;

IR 3403, 3381, 3231, 1679, 1638, 1523, 1487, $cm^{-1}$ HRMS (ESI) for $C_{28}H_{45}NO_3S$, calculated $[M+H]^+$:451.3212. Obtained: 451.3214. $^1$H NMR (400 MHz, MeOD-$d_4$) δ 12.08 (s, 1H), 8.07 (s, 1H) 4.47 (s, 1H), 3.89 (d, J=6.6 Hz, 1H), 3.50 (m, 2H), 3.34-3.26 (m, 1H), 2.24 (m, 1H), 2.14 (m, 1H), 1.99-1.90 (m, 1H), 1.92-1.76 (m, 1H), 1.70 (dd, J=7.9, 4.1 Hz, 3H), 1.46 (q, J=7.8, 6.5 Hz, 4H), 1.47-1.35 (m, 3H), 1.38-1.22 (m, 4H), 1.26-1.04 (m, 1.00 (dd, J=18.7, 9.4 Hz, 1H), 0.89 (d, J=6.6 Hz, 7H), (s, 3H). $^{13}$ C NMR (101 MHz,MeOD-d4) δ 174.88, 69.71, 69.44, 54.66, 43.08, 42.99, 42.35, 42.16, 40.17, 39.97, 39.80, 38.71, 37.71, 37.25, 34.83, 33.74, 30.76, 30.23, 28.16, 27.60, 26.70, 23.30, 20.84, 18.29, 12.02.

Example 21 (Synthesis I1)

(R)-4 -((3R,5S,7S,8R,9S,10S,13R,14S,17R)-3,7-dihydroxy-10,13-dimethylhexadecanohydro-1H-cyclopenta [a]phenanthren-17-yl)-N-(2-mercapto-phenyl)pentanamide

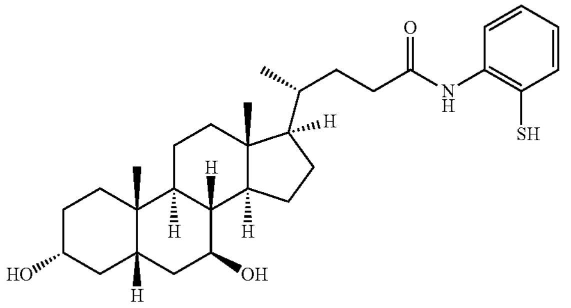

This compound was prepared following method A described above and taking into account the modifications described for the preceding example.

Ursodeoxycholic acid (250 mg, 0.63 mmol) with 2-(tritylthio)aniline hydrochloride (302.09 mg, 0.63 mmol). Brown solid. Yield 42%; Melting point 157-158° C.;

IR: 3398, 3386, 3225, 1672, 1640, 1520, 1489 $cm^{-1}$; HRMS (ESI) for $C_{26}H_{45}NO_3S$, calculated $[M+H]^+$: 499.3214. Obtained: 499.3212. $^1$H NMR (400 MHz, MeOH-$d_4$) δ 9.89 (s, 1H), 8.16 (t, J=6.0 Hz, 1H), 7 7.27 (m, 3H), 7.16 (d, J=7.9 Hz, 1H), 4.42 (sb, 1H), 3.86 (d, J=6.8 Hz, 1H), 3.29 (2H), 2.24 (m, 1H), 2.14 (m, 1H), 1.99-1.90 (m, 1H), 1.92-1.76 (m, 1H), 1.75 (dd, J=7.9, 4.1 Hz, 3H), 1.46 (q, J=7.8, 6.5 Hz, 4H), 1.47-1.35 (m, 3H), 1.38-1.24 (m, 4H), 1.26-1.08 (m, 5H), 1.02 (dd, J=18.7, 9.4 Hz, 1H), 0.87 (d, J=6.6 Hz, 7H), 0.73 (s, 3H). C NMR (101 MHz, MeO H-$d_4$) δ 172.63, 145.00, 133.00, 127.70, 126.81, 125.65, 69.46, 55.87, 54.75, 43.08, 43.01, 42.15, 41.71, 38.71, 37.71, 34.82, 33.75, 32.39, 31.69, 30.24, 28.19, 26.72, 23.31, 20.84, 18.45, 12.03

Example 22. Analysis of the Expression of Different HDAC Enzymes in Cell Cultures and Liver Tissue of Patients with Polycystic Liver Disease and Normal Individuals The expression of HDAC6 in normal and polycystic human cholangiocytes in culture was analyzed using a specific primary antibody (HDAC6 (H-300) sc-11420, Santa Cruz) and a peroxidase-conjugated secondary antibody (Sigma-Aldrich). Protein expression was quantified using a chemiluminescence system (Amersham, GE Healthcare). The GAPDH protein was used as loading control.

It has been confirmed by means of these immunoblot assays that the expression of HDAC6 is increased in polycystic human cholangiocytes (ADPKD) in comparison with normal human cholangiocytes (NHC3) (FIG. 1).

Example 23

Evaluation of the Inhibitory Activity of Compounds Ia and Ib on Different HDAC Enzymes Components of the Assay:

Peptide substrates: all HDAC assays were performed using acetylated peptide substrates labeled with 7-amino-4-methylcoumarin (AMC):

- Substrate for isoforms HDAC1, 2, 3, 6, 10, 11, and HeLa nuclear extract assays: acetylated fluorogenic peptide from p53 residues 379-382 (RHKKAc).
- Substrate for isoforms HDAC4, 5, 7, 9: fluorogenic Boc-L-Lys (s-trifluoroacetyl)-AMC.
- Substrate for HDAC8 assays: acetylated fluorogenic peptide from p53 residues 379-382 (RHKAcKAc).

Assay buffer. 50 mM Tris-HCl, pH 8.0, 137 mM NaCl, 2.7 mM KCl, 1 mM $MgCl_2$ (supplemented with 1 mg/ml of BSA for the dilution) (BioMol Cat. #KI-143).

Enzymes:

- HDAC1 assay: 75 nM human HDAC1 (GenBank accession number NM_004964): full length with GST C-terminal tag, MW=79.9 kDa, expressed by a baculovirus expression system in Sf9 cells (BioMol Cat. #SE-456).
- HDAC2 assay: 5 nM human HDAC2 (GenBank accession number Q92769): full length with His C-terminal tag, MW=60 kDa, expressed by a baculovirus expression system in Sf9 cells (BioMol Cat. #SE-500).
- HDAC3 assay: 2.3 nM human HDAC3/NcoR2 (GenBank accession number NM_003883 for HDAC3, GenBank accession number NM_006312 for NcoR2): human HDAC3 complex, full length with His C-terminal tag, MW=49.7 kDa, and human NCOR2, GST N-terminal tag, MW=39 kDa, co-expressed in a baculovirus expression system (BioMol Cat. #SE-507).
- HDAC4 assay: 266 nM human HDAC4 (GenBank accession number NM_006037): amino acids 627-1085 with GST N-terminal tag, MW=75.2 kDa, expressed in a baculovirus expression system (BioMol, Hamburg, Germany).
- HDACS assay: 588 nM human HDACS (GenBank accession number NM_001015053): full length with GST N-terminal tag, MW=150 kDa, expressed by a baculovirus expression system in Sf9 cells (BioMol, Hamburg, Germany).
- HDAC6 assay: 13 nM human HDAC6 (GenBank accession number BC069243): full length with GST N-terminal tag, MW=159 kDa, expressed by a baculovirus expression system in Sf9 cells (BioMol Cat. #SE-508).
- HDAC7 assay: 962 nM human HDAC7 (GenBank accession number AY302468): amino acids 518 end with GST N-terminal tag, MW=78 kDa, expressed in a baculovirus expression system (BioMol, Hamburg, Germany).
- HDAC8 assay: 19 nM human HDAC8 (GenBank accession number NM018486): full length, MW=42 kDa, expressed in an *E. coli* expression system (BioMol Cat. #SE-145).
- HDAC9 assay: 986 nM human HDAC9 (GenBank accession number NM178423): Amino acids 604-1066 with His C-terminal tag, MW=50.7 kDa, expressed in a baculovirus expression system (BioMol, Hamburg, Germany).
- HDAC10 assay: 781 nM human HDAC10 (GenBank accession number NM_032019): Amino acids 1-631 with GST N-terminal tag, MW=96 kDa, expressed by a baculovirus expression system in Sf9 cells (BioMol Cat. #SE-559).
- HDAC11 assay: 781 nM human HDAC11 (GenBank accession number NM_BC009676) with GST N-terminal tag, MW=66 kDa, expressed in a baculovirus expression system (BioMol Cat. #SE-560).
- HeLa cell nuclear extract assay: 25 ng/μl nuclear extract from HeLa cells: prepared by high-salt extraction of HeLa nuclei (HeLa being a human cervical cancer cell line), this extract is a rich source of HDAC activity (BioMol Cat. #KI-140).

Assay Procedure:

50 μl of peptide substrate (see "peptide substrates" section above) and an optimal concentration of the corresponding enzyme (see "enzymes" section above) in the assay buffer at a final DMSO concentration of 1% were incubated in the presence of gradient concentrations of inhibitors (10-dose IC50 mode with 3-fold serial dilution) at 30° C. for 2 hours. The reactions were carried out in a 96-well microplate for fluorometry in a 50 μl reaction volume. After the deacetylation reaction, Fluor-de-Lys-Developer (BioMol Cat. #KI-105) was added to each well to digest the deacetylated substrate, thereby producing the fluorescent signal. The reaction was carried out for 45 minutes at 30° C. with 5% CO2; the fluorescent signal was then measured using an excitation wavelength of 360 nm and an emission wavelength of 460 nm in a microplate-reading fluorometer (GeminiXS, Molecular Devices, Sunnyvale, CA). A curve of deacetylated standard (Biomol, Cat. #KI-142; made from 100 μM with 1:2 dilution and 10 doses, 6 μl) allowed the conversion of the fluorescent signal into micromoles of deacetylated product. All experiments were performed in triplicate. The IC50s were calculated by fitting the experimental data to dose-response curve. DMSO was used as negative control; Trichostatin A (Biomol Cat. #GR-309) was used as positive control inhibitor.

Enzymatic activity assays were carried out in 11 HDAC enzymes, including HDAC6.

Figure 2:
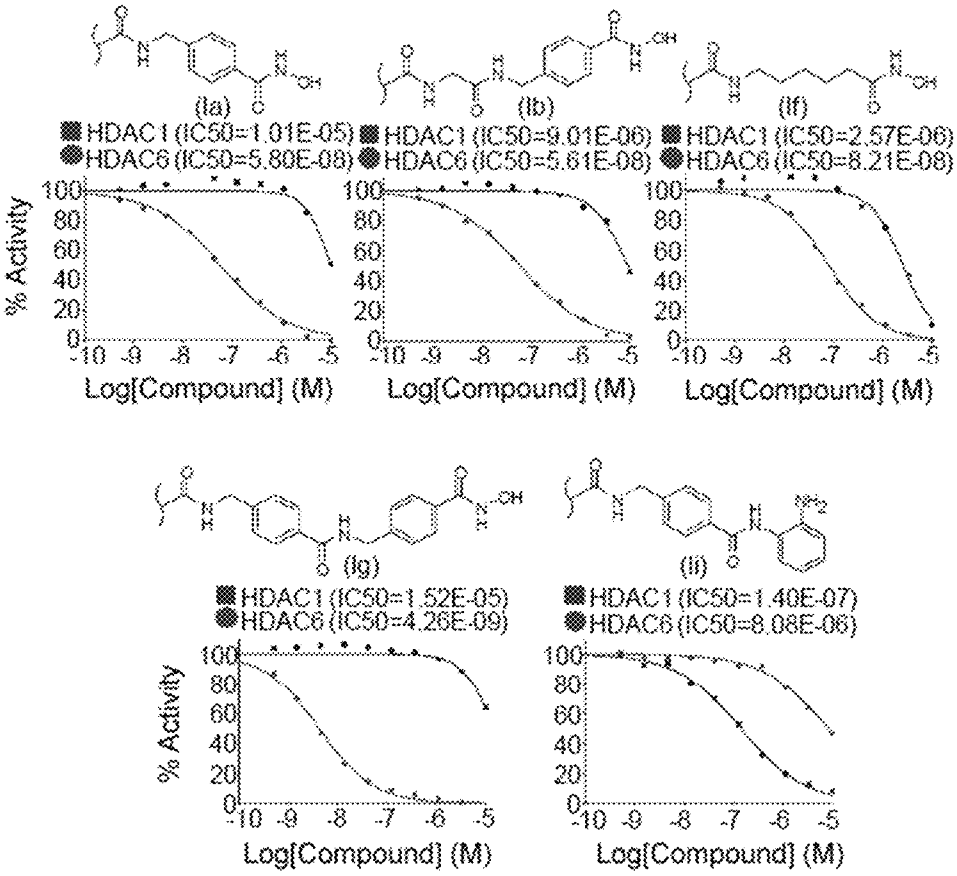
FIG. 2 shows the dose-response curves of the inhibitory effect of compounds Ia, Ib, and 4-(aminomethyl)-N-hydroxybenzamide on HDAC6.

The data obtained is shown in Table 1 and FIG. 2.

TABLE 1

IC50 of the inhibitory effect of compounds Ia, Ib, If, Ig, Ii, ursodeoxycholic acid (UDCA), and 4-(aminomethyl)-N-hydroxybenzamide on different HDAC enzymes.

| | | Compound | | | | | | |
|---|---|---|---|---|---|---|---|---|
| | | Ia | Ib | If | Ig | Ii | 4-(amino-methyl)-N-hydroxy-benzamide | UDCA |
| HDAC1 | IC50 | 1.01E−05 | 9.01E−06 | 2.57E−06 | 1.52E−05 | 1.40E−07 | ND | ND |
| HDAC2 | (M) | 1.88E−05 | 1.32E−05 | ND | ND | 5.16E−07 | ND | ND |
| HDAC3 | | 8.37E−06 | 9.99E−06 | ND | ND | ND | ND | ND |
| HDAC4 | | 1.65E−05 | ND | ND | ND | ND | ND | ND |
| HDAC5 | | 1.41E−05 | ND | ND | ND | ND | 4.35E−04 | ND |
| HDAC6 | | 5.80E−08 | 5.61E−08 | 8.21E−08 | 4.26E−09 | 8.08E−06 | 6.89E−07 | ND |
| HDAC7 | | 7.47E−06 | 1.76E−05 | ND | ND | ND | 1.47E−05 | ND |
| HDAC8 | | 8.94E−07 | 6.15E−07 | ND | ND | ND | 1.36E−05 | ND |
| HDAC9 | | 1.34E−05 | 1.16E−05 | ND | ND | ND | ND | ND |
| HDAC10 | | 2.45E−05 | 2.18E−05 | ND | ND | ND | ND | ND |
| HDAC11 | | 2.33E−06 | 2.56E−06 | ND | ND | ND | ND | ND |
| HDAC6 selectivity proportion | | 174 | 160 | 31 | 3574 | — | — | — |
| HDAC1 selectivity proportion | | — | — | — | — | 58 | — | — |

This data indicates that compounds Ia, Ib, If, and Ig have high selectivity and inhibitory capacity with respect to HDAC6 enzyme (nanomolar range) which is comparable with other HDAC6 inhibitors such as trichostatin. This inhibitory capacity is lower with respect to the rest of the HDAC enzymes (micromolar range) (Table 1), which demonstrates the selectivity thereof for HDAC6. On the other hand, the results that are obtained show that ursodeoxycholic acid has no inhibitory activity whatsoever on any HDAC in the assayed concentration range (Table 1). In the case of 4-(aminomethyl)-N-hydroxybenzamide (present in Ia, Ib, and Ig), although this compound showed certain inhibitory activity on HDAC6 with an IC50 of 6.89E-07, said activity is considerably increased after the coupling of this chemical entity to ursodeoxycholic acid (Ia) and glycoursodeoxycholic acid (Ib).

ND.: Not determined

Example 24

Figure 3:
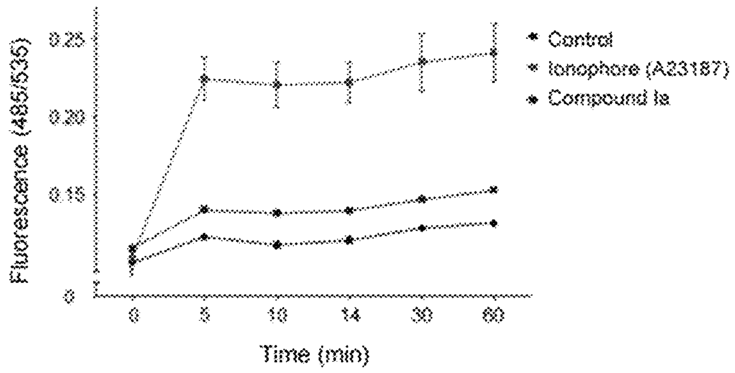
FIG. 3 shows the intracellular $Ca^{2+}$ levels in polycystic human cholangiocytes.

Study of the Effect of Compounds Ia and Ib on Intracellular $Ca^{2+}$ Levels in Polycystic Human Cholangiocytes in Vitro As described previously [Banales J M et al. Hepatology 2009; Perugorria M J et al. Nature Reviews G&H; Munoz-Garrido P et al. Journal of Hepatology 2015], polycystic (human and rat) cholangiocytes are characterized by a decrease in intracellular $Ca^{2+}$ levels, which promotes their proliferation. Furthermore, it has been proven that chronic treatment with UDCA is capable of partially inhibiting the proliferation of polycystic human cholangiocytes through the normalization of intracellular $Ca^{2+}$ levels in experimental models [Munoz-Garrido P et al. Journal of Hepatology 2015] and patients [D'Agnolo HMA, et al. Journal of Hepatology 2016] with PLD. To that end, it has been evaluated if the new chemical entities Ia and Ib (FIG. 3 only shows the result for Ia) maintain the intrinsic $Ca^{2+}$ regulatory properties of UDCA when their hydrocarbon backbone is not modified. To that end, the "Fluo-4 AM" (Thermo Fisher Scientific) intracellular $Ca^{2+}$ measurement method was used. A $Ca^{2+}$ ionophore (i.e., A23187, Sigma) was used as positive control. The data that was obtained indicated that the new chemical entities, compounds Ia and Ib, maintain the $Ca^{2+}$ modulatory properties of UDCA by increasing intracellular $Ca^{2+}$ levels in polycystic human cholangiocytes (FIG. 3).

Example 25

Determination of the Molecular Uptake Mechanisms (Vectorization/Transport) of Compound Ia in Normal and Polycystic Human Cholangiocytes In Vitro The bile acid and organic cation transporters expressed in hepatocytes and cholangiocytes were overexpressed in HepG2 cells (OCT1) and CHO cells (OCT3). The efficacy of the process was confirmed by means of measuring the abundance of mRNA (qPCR), protein (WB), and the correct insertion in the plasma membrane (immunofluorescence). The uptake studies included comparing the uptake efficiency of the compound with respect to dihydroethidium (DHE) in the case of OCT3, and sorafenib in the case of OCT1 (positive controls), as well as the sensitivity of the process to substrate inhibition induced by the joint administration of the compound and quinine. The cell content of all the compounds was determined by means of triple quadrupole HPLC-MS/MS after extraction thereof from the cell system used in each case.

The analysis of transporter expression levels (mRNA) was carried out in normal and polycystic human cholangiocytes in culture by means of qPCR using 7300 Real Time PCR System (Applied Biosystem). To that end, corresponding (sense and antisense) primers were used for amplifying specific cDNA fragments using the iQ™ SYBR® Green Supermix kit (BIO-RAD). The expression of the RPL22 gene was used as internal loading control for normalizing the expression of each sample.

Figure 4:
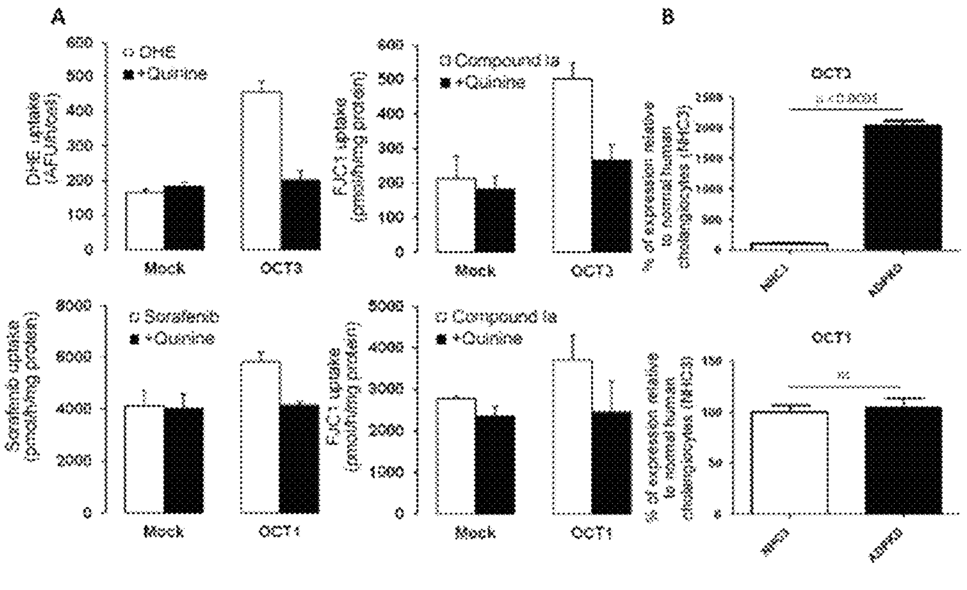
FIG. 4 shows the vectorization studies of compound Ia and the analysis of transporter gene expression. A) Study of the transport of compound Ia through transporters OCT1 and OCT3. B) Gene expression levels of transporters OCT1 and OCT3 in normal human cholangiocytes (NHC3) and polycystic human cholangiocytes (ADPKD).

The data indicated that like the drug Sorafenib, compound Ia is specifically transported through OCT1 in liver cells (FIG. 4A), but not through ASBT or OATP1B1 (data not shown), and said effect is inhibited by the presence of quinine (OCT1 inhibitor).

This was associated with an increase in OCT3 at the mRNA level in polycystic human cholangiocytes (ADPKD) in comparison with normal human cholangiocytes (NHC) (FIG. 4B,C); in contrast, changes in the expression of OATP2B1, NTCP, and ASBT were not observed between both cell types (data not shown).

Example 26

Evaluation of the Role of Compound Ia in the Proliferation of Normal and Polycystic Human Cholangiocytes In Vitro The proliferation of polycystic human cholangiocytes at 48 hours in the absence or presence of different doses of compound Ia (10, 50, 100, μM) in a quiescence culture medium was analyzed. To that end, the CFSE proliferation protocol (Invitrogen) was used using flow cytometry. The preliminary data that is obtained shows that the new chemical entity Ia inhibits the proliferation of polycystic human cholangiocytes in a dose-dependent manner (10, 50, 100 μM) and with a higher intensity than UDCA (100 μM) (FIG. 5).

Figure 5:
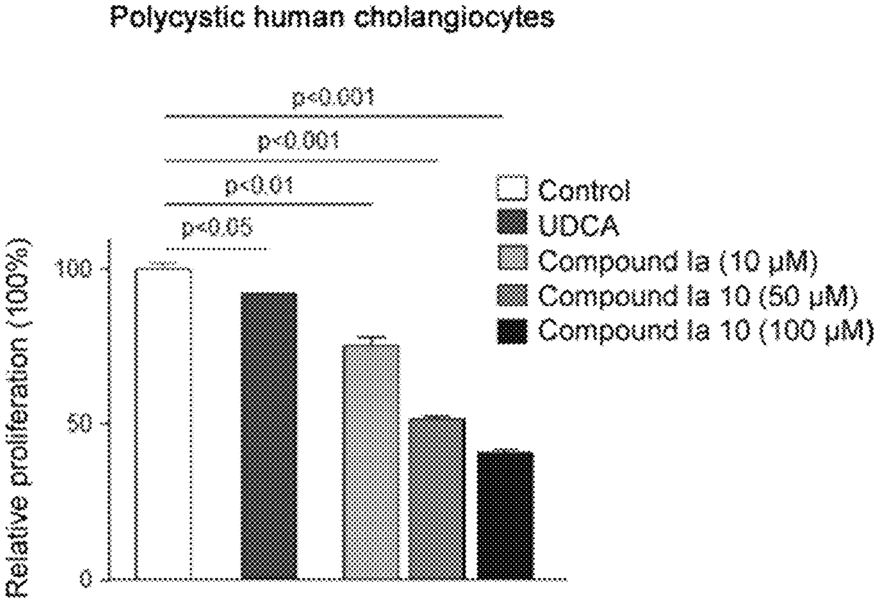
FIG. 5 shows the proliferation of polycystic human cholangiocytes cultured in the presence of different doses of compound Ia.

The data that is obtained shows that compound Ia inhibits the hyper-proliferation of polycystic human cholangiocytes in vitro in a dose-dependent manner (FIG. 5).

The expression of α-acetylated-tubulin (Ac-α-tubulin) and lysine 9-acetylated histone 3 (Ac-H3K9) in polycystic human cholangiocytes in culture was analyzed using Ac-α-tubulin-specific primary antibodies (1:2000, Sigma-Aldrich) and H3K9-specific primary antibodies (1:500, Cell Signaling Technology) and a peroxidase-conjugated secondary antibody (1:5000, Sigma-Aldrich). The expression of each protein was quantified using a chemiluminescence system (Amersham, GE Healthcare). The GAPDH protein was used as loading control.

Figure 6:
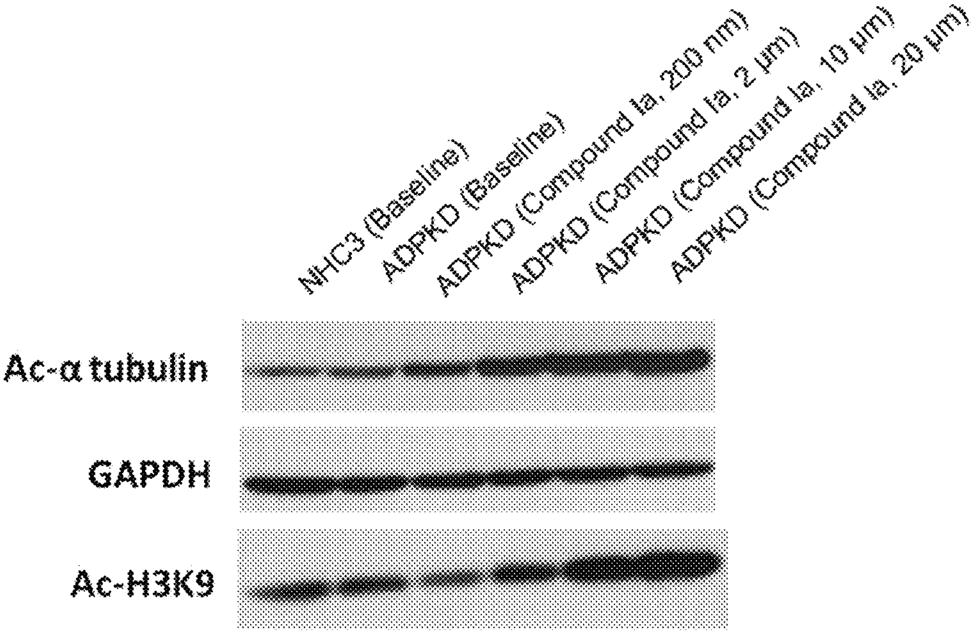
FIG. 6 shows the representative immunoblot of the levels of α-acetylated-tubulin (α-Ac-tubulin) and lysine-9-acetylated histone 3 (H3K9) in polycystic human cholangiocytes in culture treated with different doses of compound Ia.

It has been proven by means of immunoblot that the expression of α-acetylated-tubulin increases significantly and in a dose-dependent manner in the presence of compound Ia (FIG. 6).

Figure 7:
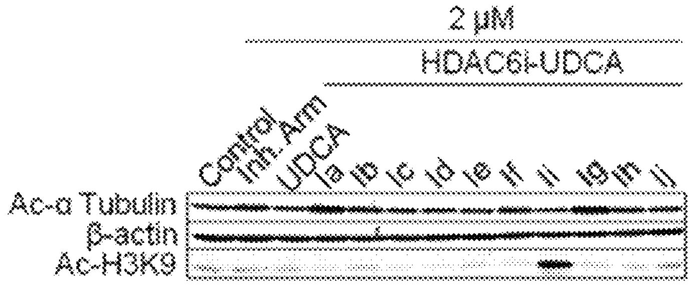
FIG. 7 shows the representative immunoblot of the acetylation levels of α-tubulin and histone 3 after treatment with each of compounds Ia-Ij.

Furthermore, the expression of α-acetylated-tubulin and acetylated histone 3 with each of the compounds of the invention (Ia-Ij) has also been analyzed. FIG. 7 shows the acetylation levels of α-tubulin and histone 3 after treatment with each of the compounds.

The expression of Ac-α tubulin and H3K9 was analyzed as described for FIG. 6, with the difference being that the protein β-actin was used in this case as loading control.

Example 27

Study of the Biodistribution and Hepatotropic Properties of Compound Ia After the Administration Thereof to Normal and PCK Rats (Animal Model of PLD)

PCK rats were chronically treated (2 months) with compound Ia (7 mg/kg/day). The data indicated that chronic treatment with compound Ia significantly reduced the levels of liver transaminase ALT, i.e., a liver damage marker which is increased at a basal level in PCK rats. This data indicates that compound Ia may be promoting a hepatoprotective effect in PCK rats.

Example 28

Analysis of the Effect of Compound Ia on the Morphology of the Primary Cilia of Polycystic Human Cholangiocytes In Vitro Cilium staining. Cells cultured on cover slips were washed with PBS, fixed with methanol, and blocked for one hour in a blocking buffer at room temperature. The γ-tubulin primary antibodies (1:100; Sigma-Aldrich, St Louis, MO) and acetylated α-tubulin primary antibodies (1:1000; Sigma-Aldrich) or IFT88 primary antibodies (1:100; ProteinTech, Rosemont, IL, USA) were incubated overnight at 4° C. After washing, Alexa Fluor 594 and 488 secondary antibodies were combined with the primary antibodies (Life Technologies, Carlsbad, CA, USA) and incubated for 2 hours at room temperature. The cover slips were placed on slides with Prolong Gold Antifade with Dapi (Invitrogen, Carlsbad, CA, USA). The slides were observed and images were taken using laser scanning confocal microscopy with a 60× objective (NIKON Clsi Confocal Spectral Imaging System, NIKON Instruments Co., Melville, NY, USA). The field was magnified 4× to observe individual cilia. The images were opened with EZ-C1 3.90 Freeviewer and a scale bar was added. The images were converted to Tiff files and quantified using ImageJ Software. The scale bar saved in the image was measured and the scale established. Using the freehand tool, the cilia were traced and measurements taken.

Figure 8:
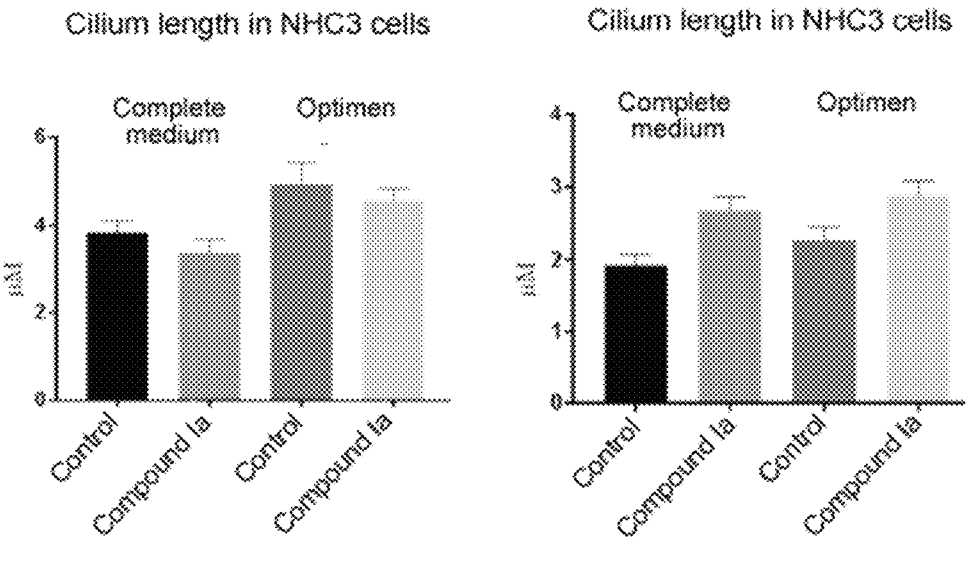
FIG. 8 shows the quantitative analysis of the cilium length in cell cultures of normal and polycystic human cholangiocytes.

On the other hand, it has been observed that the baseline length of the cilia of normal human cholangiocytes (NHC3) is greater than that of the cilia present in polycystic human cholangiocytes. This length is significantly increased after treatment of the polycystic human cholangiocytes with compound Ia. On the other hand, treatment of the normal human cholangiocytes with compound Ia did not lead to any significant variations in the length of the cilia in these cells (FIG. 8).

The invention claimed is:

1. A compound of formula (I'):

(I')

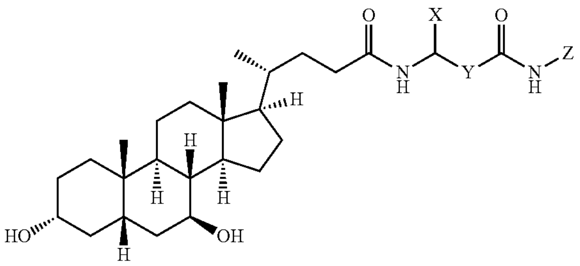

wherein:

X is hydrogen or a $C_6$-$C_{10}$ aryl group;

Y is selected from:

—$(CH_2)_n$, wherein n is 1-5;

arylidene or heteroarylidene, wherein the arylidene or heteroarylidene are connect by (1,3) or (1,4) bonds;

—C(O)—N(H)—$CH_2$ (Ar)—, or

—Ar—C(O)—N(H)—$CH_2$—(Ar)—, wherein Ar is arylidene and

Z is selected from OH and optionally substituted $C_6$-$C_{10}$ aryl, or a pharmaceutically acceptable stereoisomer, salt, or solvate thereof.

2. The compound according to claim 1, wherein X is hydrogen.

3. The compound according to claim 1, wherein Y is arylidene or heteroarylidene.

4. The compound according to claim 1, wherein Y is —$(CH_2)_n$, where n is 1, 2, 3, or 4.

5. The compound according to claim 1, wherein Z is OH or the optionally substituted $C_6$-$C_{10}$ aryl substituted by at least one of $NH_2$ and a phenyl.

6. The compound according to claim 1 selected from:

(Ia)

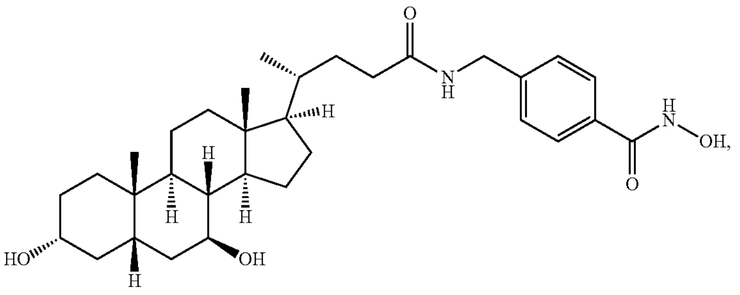

(Ib)

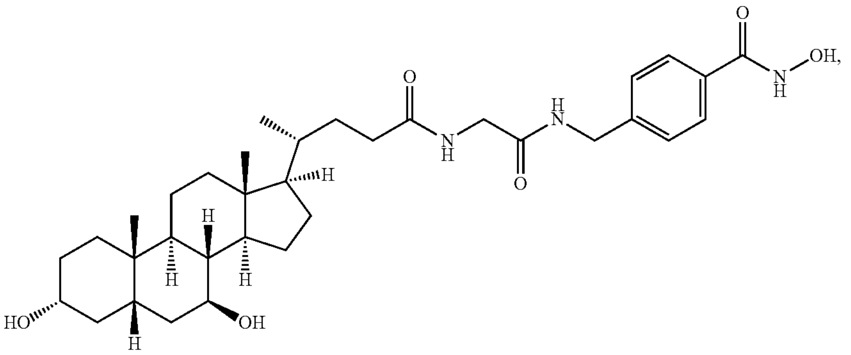

(Id)

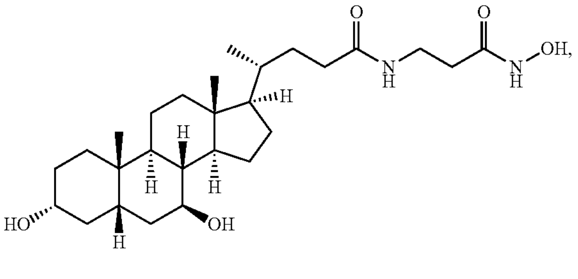

(Ie)

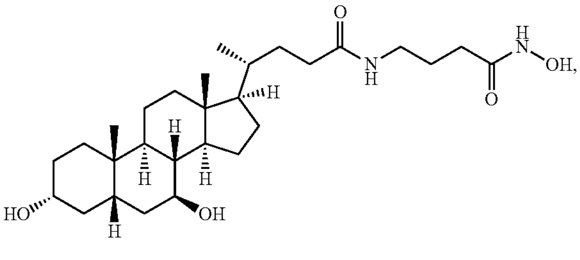

(If)

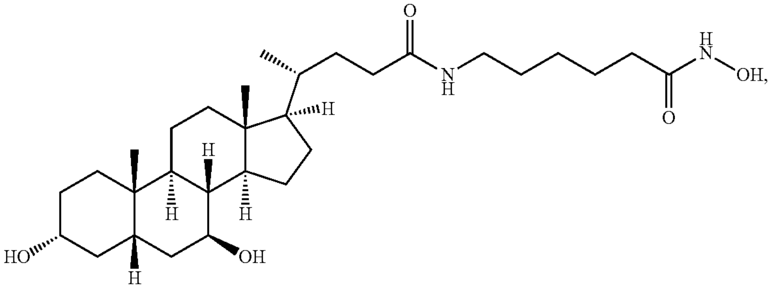

-continued
(Ig)
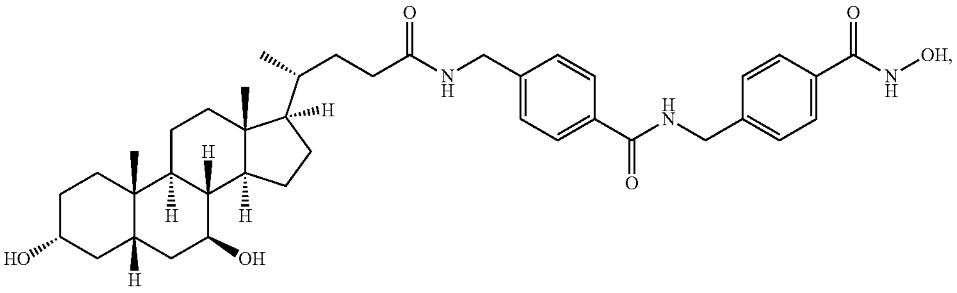
(Ih)
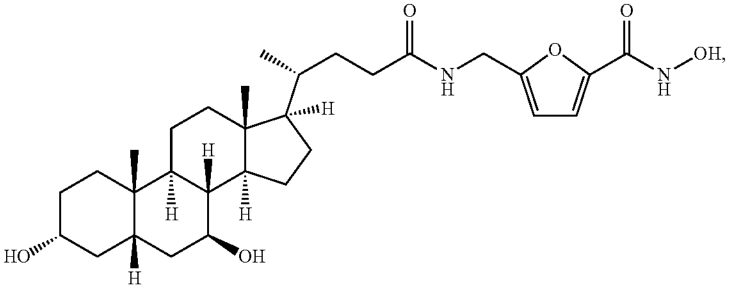
(Ii)
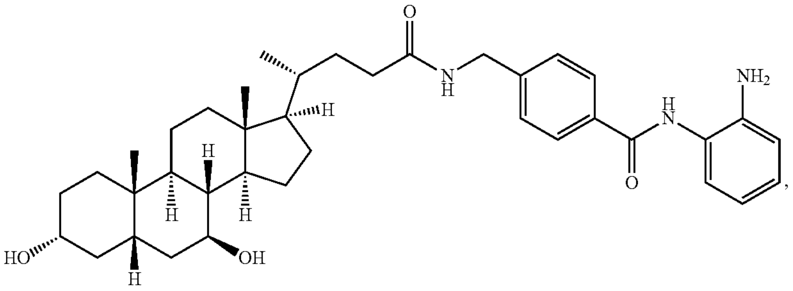
(Ij)
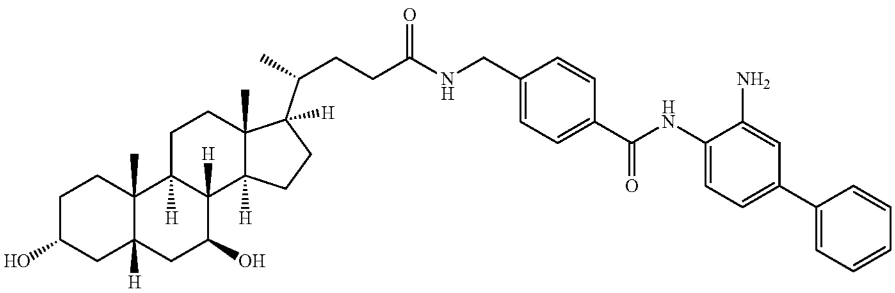

7. A pharmaceutical composition comprising a compound of formula (I') according to claim 1, or a stereoisomer, a salt, or a solvate thereof, and a pharmaceutically acceptable excipient or vehicle.

8. A process for obtaining compounds of formula (I') according to claim 1, comprising:

reacting ursodeoxycholic acid of formula (II):

(II)

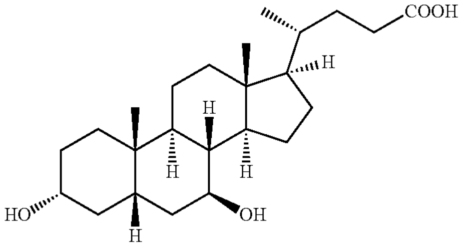

with a compound of formula (III'):

(III')

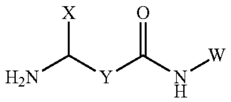

wherein:

X is hydrogen or a $C_6$-$C_{10}$ aryl group;

Y is selected from:

—$(CH_2)_n$, wherein n is 1-5;

arylidene or heteroarylidene, wherein the arylidene or heteroarylidene are connect by (1,3) or (1,4) bonds;

—C(O)—N(H)—$CH_2$ (Ar)—, or

—Ar—C(O)—N(H)—$CH_2$—(Ar)—, wherein Ar is arylidene and where W is a precursor group of groups Z defined in claim 1, and subsequently transforming groups W into the corresponding groups Z of formula (I').

* * * * *